United States Patent
Deslauriers

[11] Patent Number: 6,149,653
[45] Date of Patent: Nov. 21, 2000

[54] SELF-RETAINING ANCHOR TRACK AND METHOD OF MAKING AND USING SAME

[76] Inventor: Richard J. Deslauriers, 78 Joseph St., Waterbury, Conn. 06705

[21] Appl. No.: 09/148,402

[22] Filed: Sep. 4, 1998

Related U.S. Application Data

[60] Provisional application No. 60/057,656, Sep. 5, 1997, provisional application No. 60/073,381, Feb. 2, 1998, and provisional application No. 60/077,449, Mar. 10, 1998.

[51] Int. Cl.⁷ .................................................. A61B 17/56
[52] U.S. Cl. ............................................ 606/72; 606/232
[58] Field of Search ................................ 606/72, 68–71, 606/73–75, 104–105, 232; D8/385–395; 411/57–60, 44, 33, 71, 395, 426, 308–311

[56] References Cited

U.S. PATENT DOCUMENTS

| D. 200,218 | 2/1965 | Curtiss ....................................... D8/378 |
| D. 378,052 | 2/1997 | Perreault ................................... D8/378 |
| D. 385,352 | 10/1997 | Bales et al. . |
| 4,130,152 | 12/1978 | Bolen . |
| 4,632,100 | 12/1986 | Somers et al. . |
| 4,711,232 | 12/1987 | Fischer et al. . |
| 4,738,255 | 4/1988 | Goble et al. . |
| 4,870,957 | 10/1989 | Goble et al. . |
| 4,898,156 | 2/1990 | Gatturna et al. . |
| 4,899,743 | 2/1990 | Nicholson et al. . |
| 4,911,593 | 3/1990 | Kephart . |
| 4,946,468 | 8/1990 | Li . |
| 4,968,315 | 11/1990 | Gatturna . |
| 5,002,550 | 3/1991 | Li . |
| 5,013,316 | 5/1991 | Goble et al. . |
| 5,019,078 | 5/1991 | Perren et al. . |
| 5,037,422 | 8/1991 | Hayhurst et al. . |
| 5,046,513 | 9/1991 | Gatturna et al. . |
| 5,061,181 | 10/1991 | Niznick . |
| 5,078,607 | 1/1992 | Niznick . |
| 5,080,543 | 1/1992 | Murphy . |

(List continued on next page.)

FOREIGN PATENT DOCUMENTS

| 0230678 | 1/1986 | European Pat. Off. . |
| 0236698 | 1/1987 | European Pat. Off. . |
| 0240034 | 4/1987 | European Pat. Off. . |
| 0317688 | 11/1987 | European Pat. Off. . |
| 0291632 | 2/1988 | European Pat. Off. . |
| 0325682 | 6/1988 | European Pat. Off. . |
| 0320740 | 12/1988 | European Pat. Off. . |
| 0323823 | 12/1988 | European Pat. Off. . |
| 0436885 | 12/1990 | European Pat. Off. . |
| 0445667 | 3/1991 | European Pat. Off. . |
| 0530160 | 7/1992 | European Pat. Off. . |
| 0537571 | 10/1992 | European Pat. Off. . |
| 0547380 | 11/1992 | European Pat. Off. . |
| 8905677 | 7/1989 | Germany . |
| 18027 | 4/1911 | United Kingdom . |
| 2244775 | 12/1991 | United Kingdom . |

*Primary Examiner*—Michael Buiz
*Assistant Examiner*—Lien Nao
*Attorney, Agent, or Firm*—Baker Botts L.L.P.

[57] ABSTRACT

A suture anchor, self-retaining bone screw and method of making and using them are disclosed. The suture anchor includes a track within which a suture may be anchored. The suture anchor track may be incorporated underneath the head of a bone screw in general alignment with a slot used to drive the bone screw, so that the track is accessible through the slot. In operation, suture is slid down into the slot and over and up into the track. The self-retaining screw includes at least one spring arm that provides a locking force when engaged with a driver. A method of making the anchor track and self-retaining component is also disclosed. The method comprises positioning a screw blank and using an EDM process to cut a slot and an internal track into the head portion of the screw blank.

91 Claims, 33 Drawing Sheets

U.S. PATENT DOCUMENTS

| | | |
|---|---|---|
| 5,100,417 | 3/1992 | Cerier et al. . |
| 5,102,421 | 4/1992 | Anspach, Jr. . |
| 5,141,520 | 8/1992 | Goble et al. . |
| 5,156,616 | 10/1992 | Meadows et al. . |
| 5,169,400 | 12/1992 | Mühling et al. . |
| 5,180,382 | 1/1993 | Frigg et al. . |
| 5,192,303 | 3/1993 | Gatturna et al. . |
| 5,207,679 | 5/1993 | Li . |
| 5,209,753 | 5/1993 | Biedermann et al. . |
| 5,217,486 | 6/1993 | Rice et al. . |
| 5,224,946 | 7/1993 | Hayhurst et al. . |
| 5,236,445 | 8/1993 | Hayhurst et al. . |
| 5,258,016 | 11/1993 | DiPoto et al. . |
| 5,269,685 | 12/1993 | Jorneus et al. . |
| 5,334,204 | 8/1994 | Clewett et al. . |
| 5,346,492 | 9/1994 | Morgan ................ 606/69 |
| 5,354,299 | 10/1994 | Coleman . |
| 5,364,400 | 11/1994 | Rego, Jr. et al. . |
| 5,370,662 | 12/1994 | Stone et al. . |
| 5,391,170 | 2/1995 | McGuire et al. . |
| 5,409,486 | 4/1995 | Reese . |
| 5,411,523 | 5/1995 | Goble . |
| 5,423,860 | 6/1995 | Lizardi et al. . |
| 5,443,482 | 8/1995 | Stone et al. . |
| 5,454,811 | 10/1995 | Huebner . |
| 5,456,685 | 10/1995 | Huebner . |
| 5,464,427 | 11/1995 | Curtis et al. . |
| 5,480,403 | 1/1996 | Lee et al. . |
| 5,484,440 | 1/1996 | Allard . |
| 5,486,197 | 1/1996 | Le et al. . |
| 5,501,683 | 3/1996 | Trott . |
| 5,522,845 | 6/1996 | Wenstrom, Jr. . |
| 5,527,342 | 6/1996 | Pietrzak et al. . |
| 5,534,011 | 7/1996 | Greene, Jr. et al. . |
| 5,545,180 | 8/1996 | Le et al. . |
| 5,562,547 | 10/1996 | Borzone . |
| 5,569,306 | 10/1996 | Thal . |
| 5,571,073 | 11/1996 | Castillo . |
| 5,571,139 | 11/1996 | Jenkins, Jr. . |
| 5,573,548 | 11/1996 | Nazre et al. . |
| 5,578,034 | 11/1996 | Estes . |
| 5,584,835 | 12/1996 | Greenfield . |
| 5,584,836 | 12/1996 | Ballintyn et al. . |
| 5,634,925 | 6/1997 | Urbanski . |
| 5,645,546 | 7/1997 | Fard . |
| 5,662,651 | 9/1997 | Tornier et al. . |
| 5,681,319 | 10/1997 | Biedermann et al. . |
| 5,868,749 | 2/1999 | Reed ................ 606/73 |
| 5,928,236 | 7/1999 | Augagneur et al. ........ 606/73 |

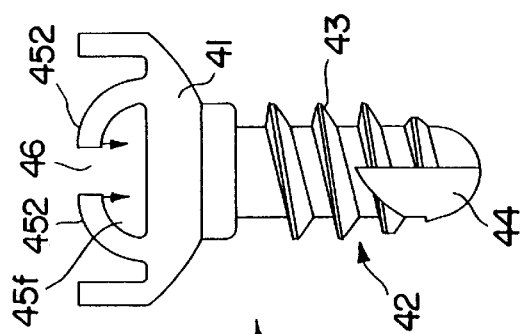
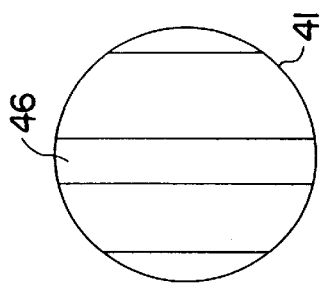
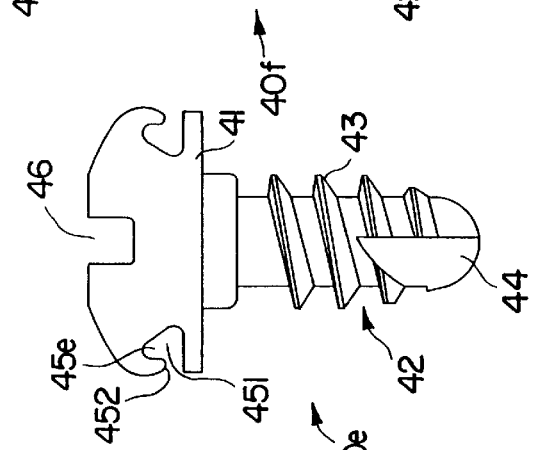
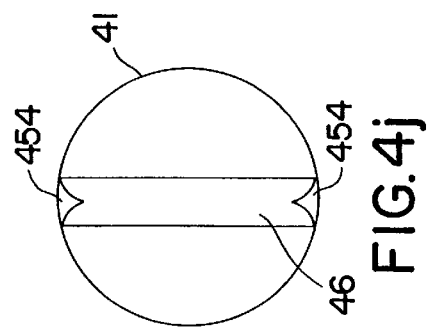
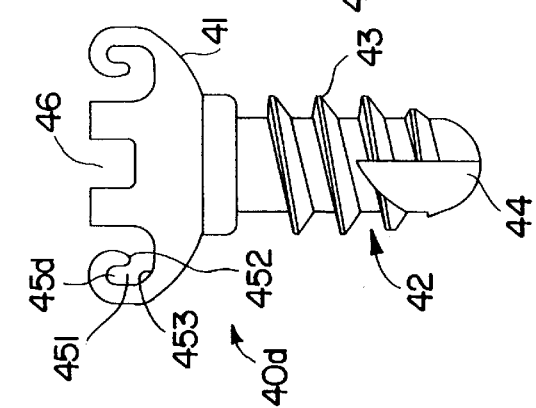
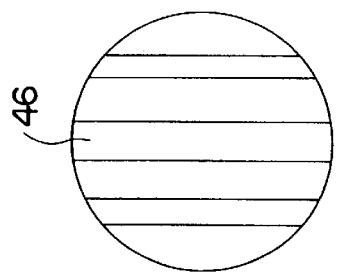
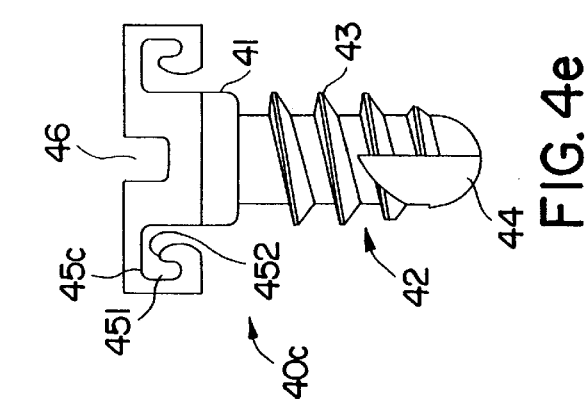
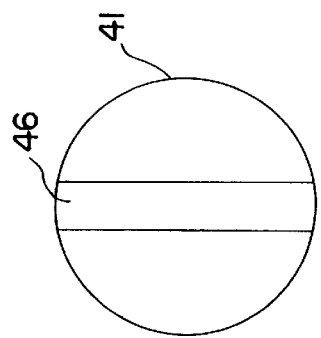

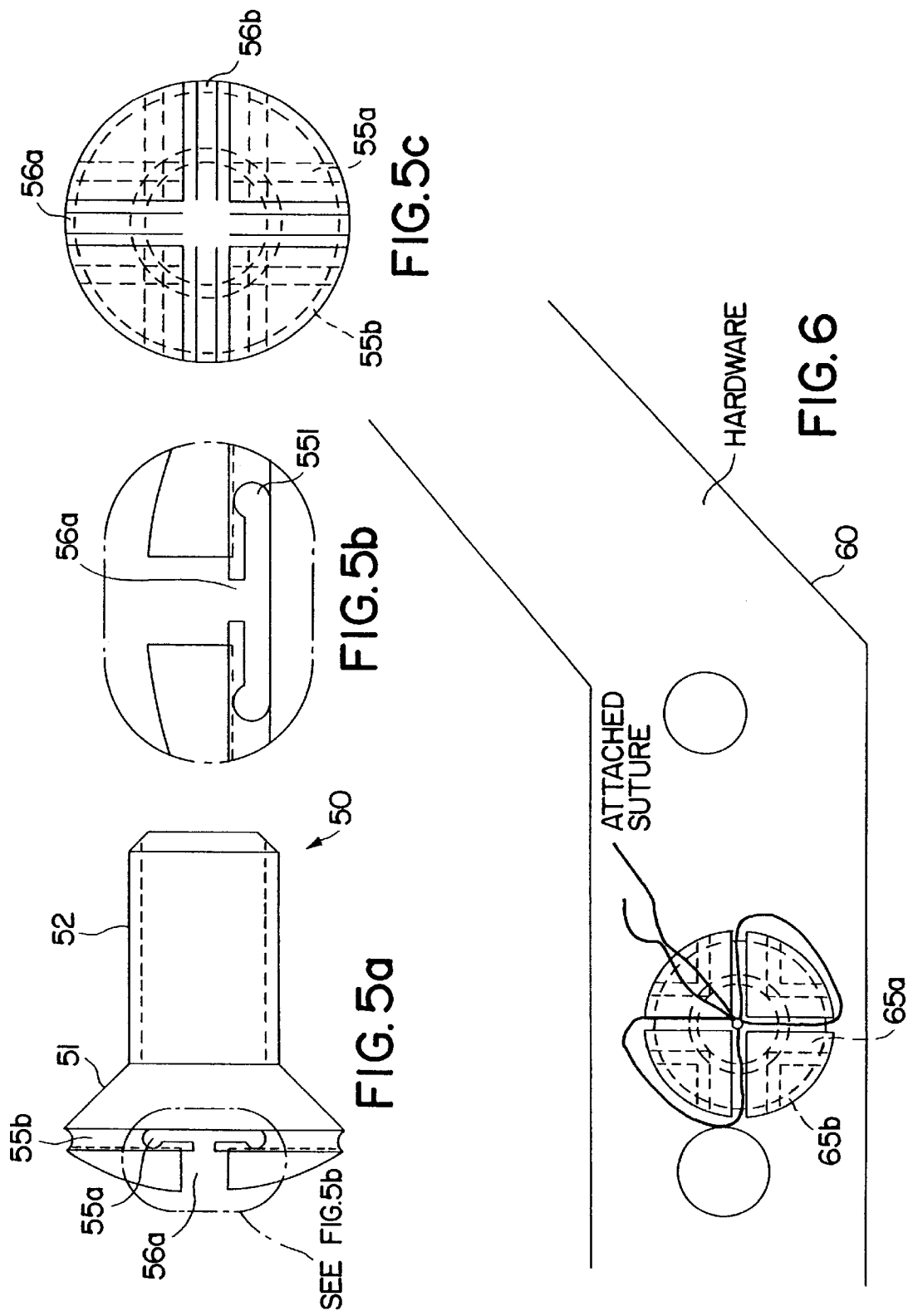

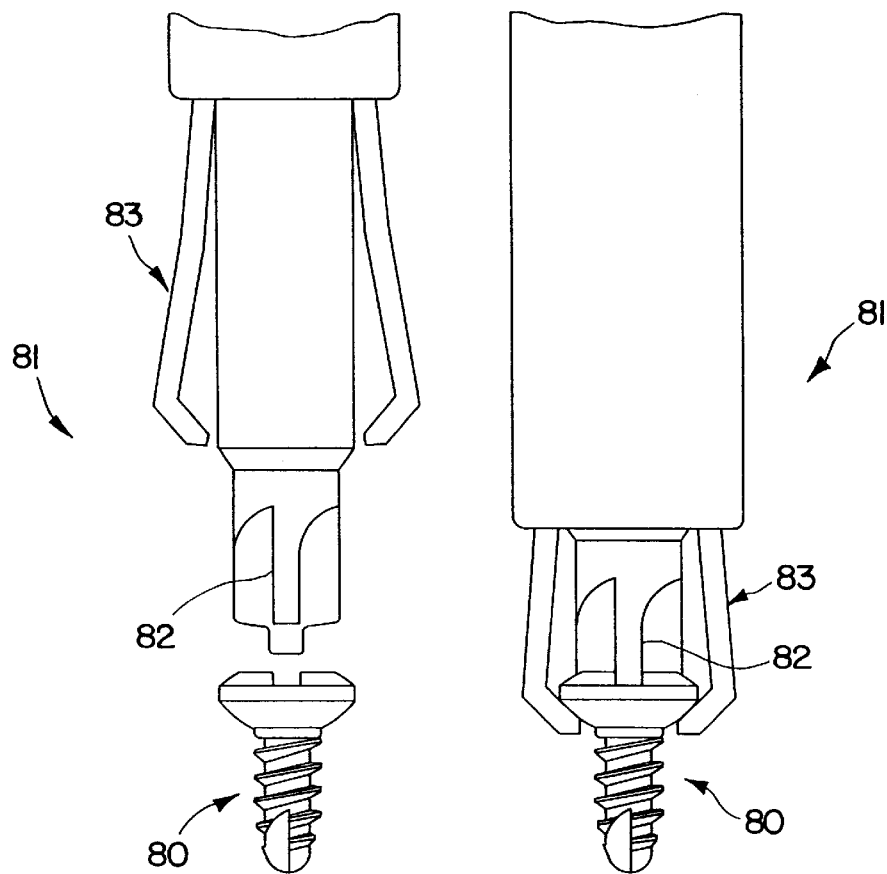
FIG. 8a
PRIOR ART
FIG. 8b
PRIOR ART
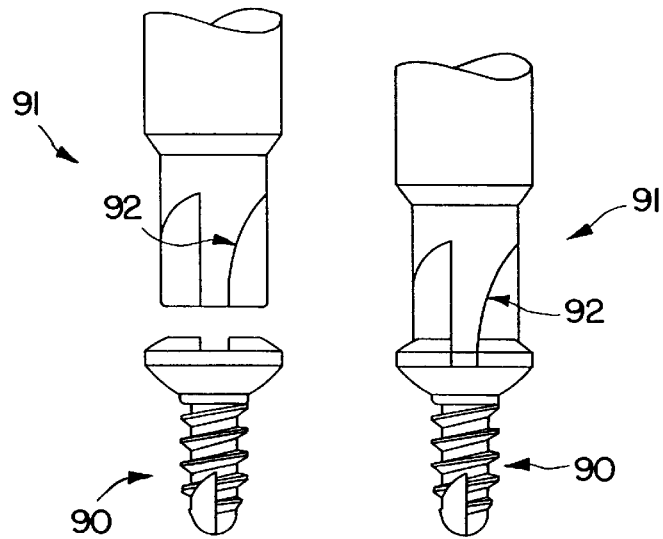
FIG. 9a
PRIOR ART
FIG. 9b
PRIOR ART

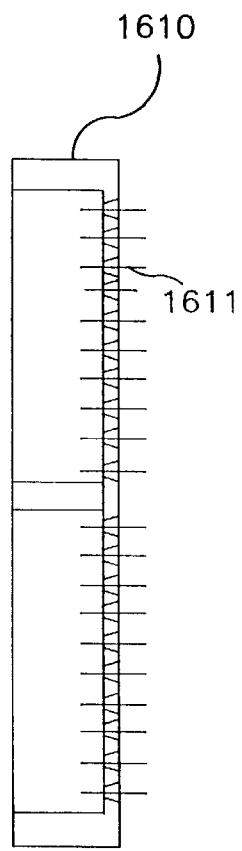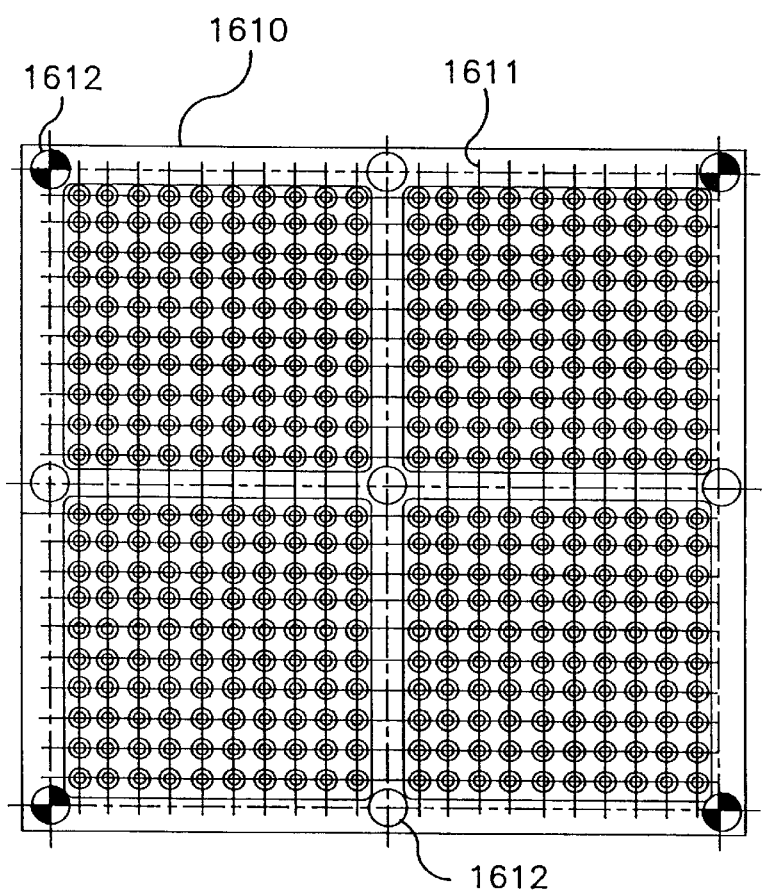
FIG. 16b
FIG. 16a

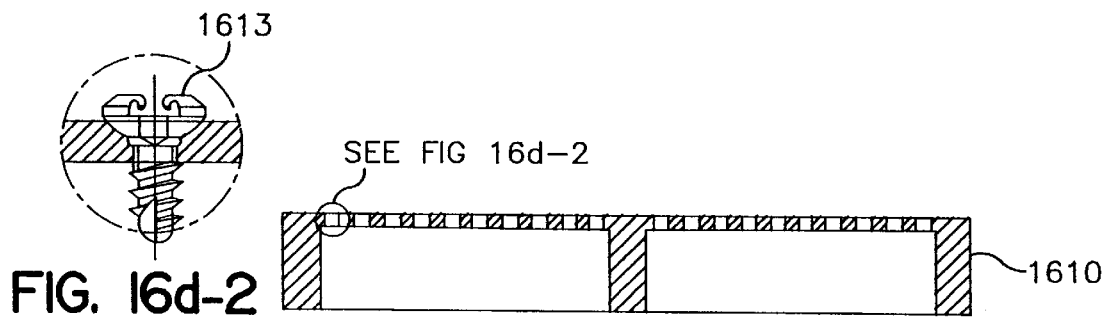
FIG. 16d-2
FIG. 16d-1
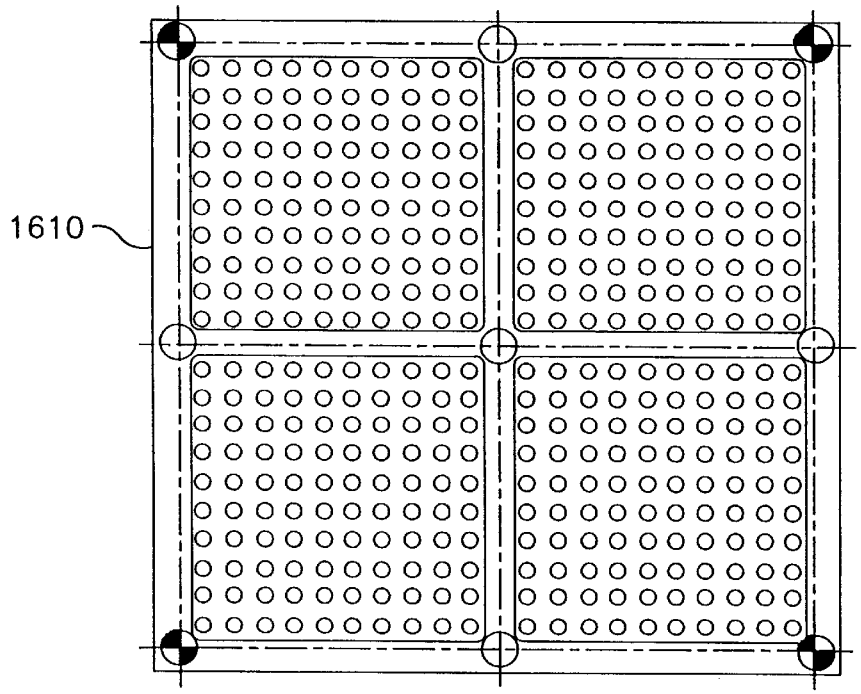
FIG. 16c

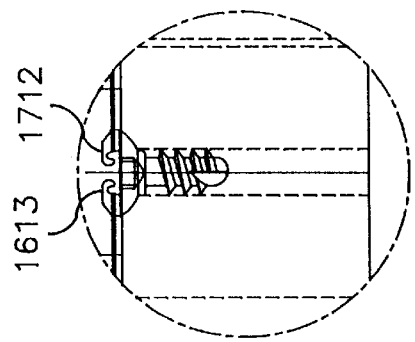
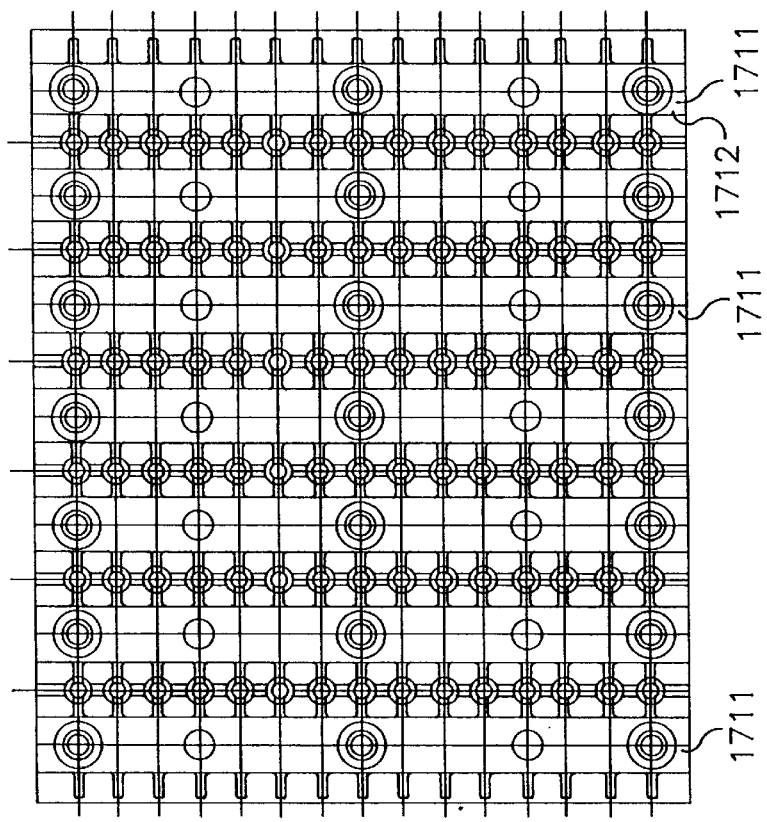
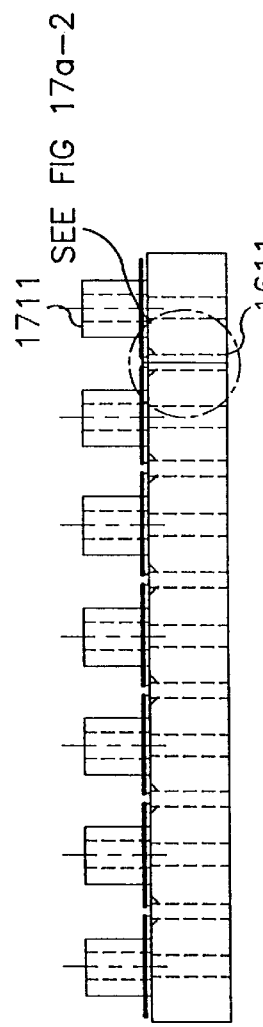

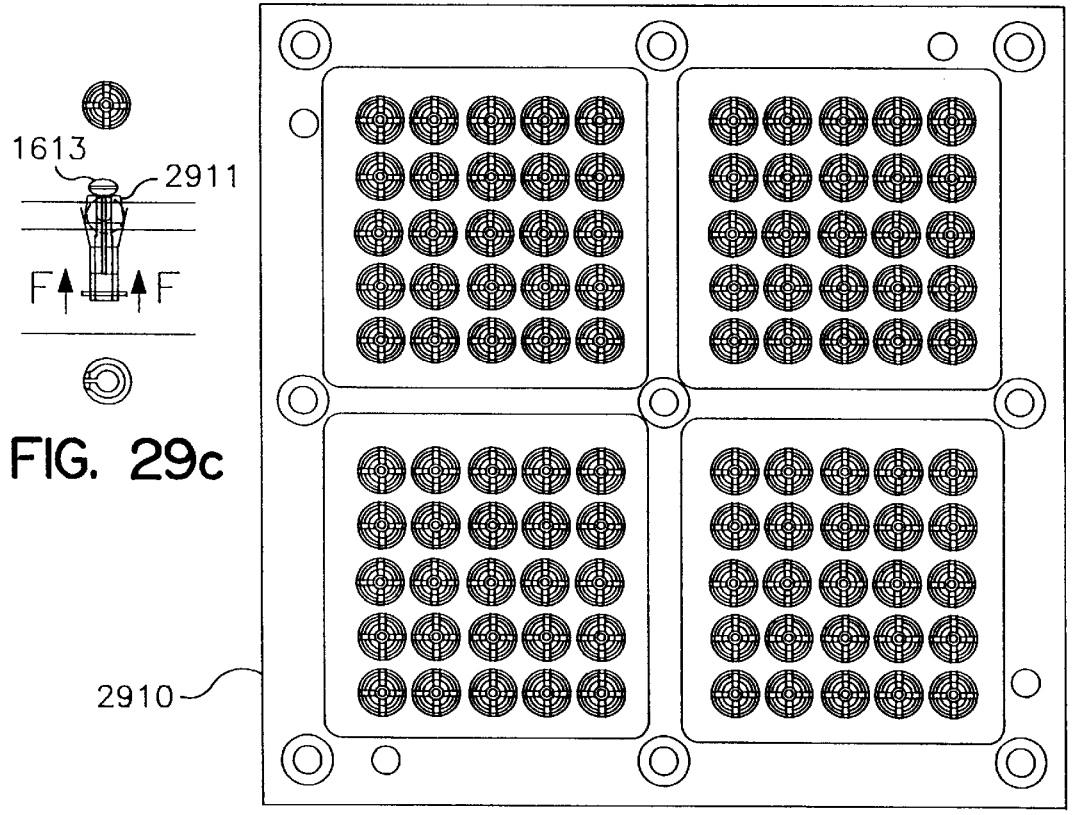
FIG. 29c
FIG. 29a
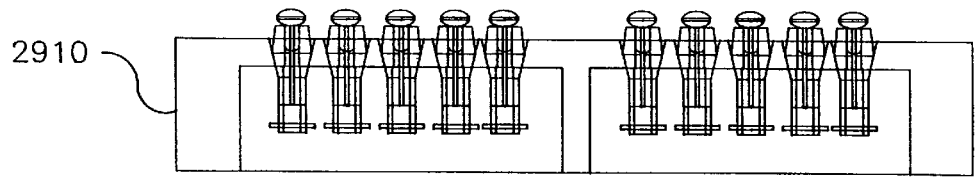
FIG. 29b

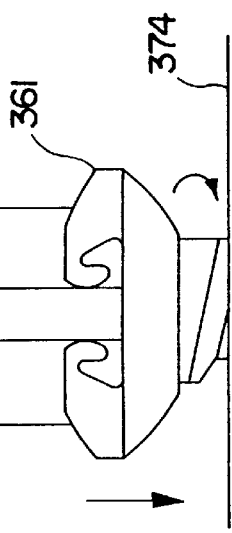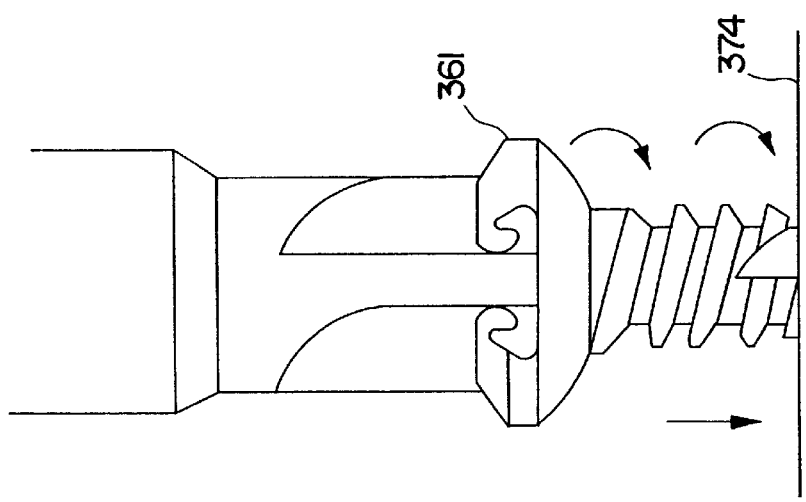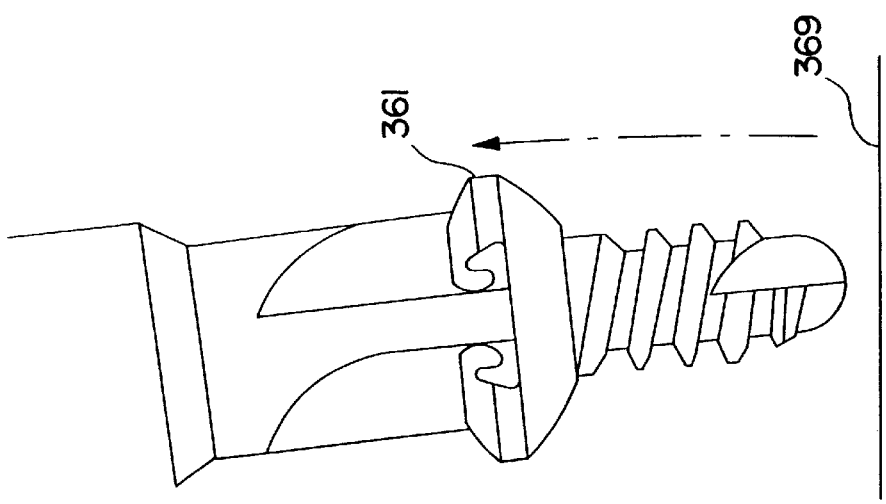

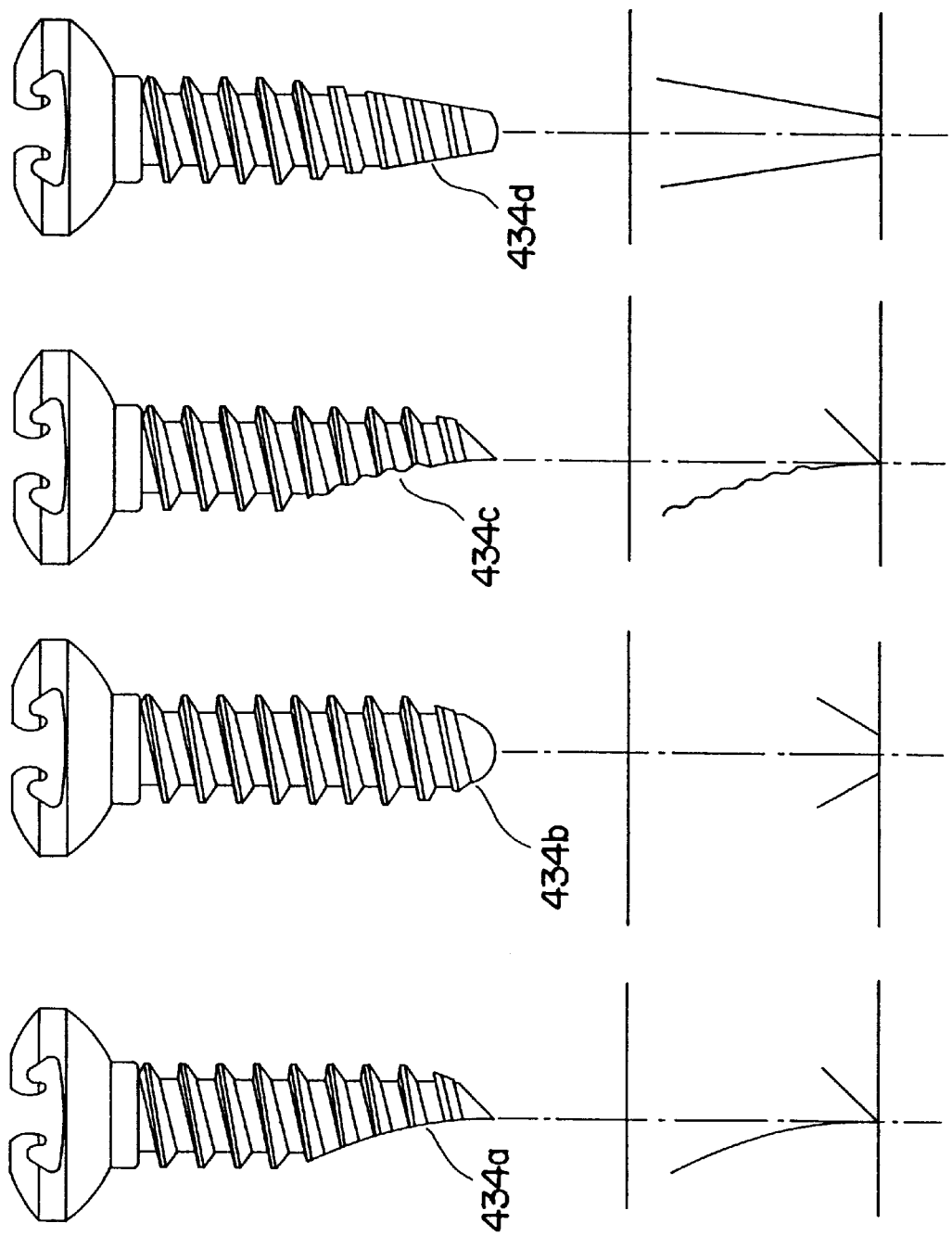

SELF-RETAINING ANCHOR TRACK AND METHOD OF MAKING AND USING SAME

This application claims benefit of provisional applications Ser. Nos. 60/057656, filed Sep. 5, 1997, 60/073381, filed Feb. 2, 1998, 60/077449, filed Mar. 10, 1998.

TECHNICAL FIELD OF THE INVENTION

This invention relates generally to the field of mechanical fasteners such as self-retaining screws, self-retaining bone screws, anchors, and suture anchors and more particularly to a track and a process for fabricating the track into general hardware.

BACKGROUND OF THE INVENTION

Mechanical fasteners are used to connect or attach. Bone screws and suture anchors are used pervasively in the treatment of fractured bones and in wound closures and during the course of surgical procedures to secure and/or attach things. During the course of a surgical procedure, a suture is typically anchored to enable it to better perform its function of attaching or securing. That is, one end of a suture is attached to some substrate and the other end is used to secure or attach a desired object to the substrate. In a typical example, a suture is used to attach a tendon to a bone that it has become detached from. Sutures are also used to attach or secure muscles, ligaments, tissue and prostheses during the course of a surgical procedure. Screws are generally used to secure surgical plates to provide rigid fixation of bones.

Numerous devices such as, inter alia bone screws, staples, anchors, and rivets are used to anchor sutures. Often these devices are inserted into a hole formed in a substrate, such as, a bone, and secured within the hole through barbs, fins, ribs, or some other securing mechanism which "digs into" or causes friction with the surrounding bone. Examples of such devices are described in U.S. Pat. No. 4,898,156; U.S. Pat. No. 5,037,422; U.S. Pat. No. 5,217,486; and U.S. Pat. No. 5,486,197. These devices suffer from various drawbacks.

One drawback is that these devices are difficult to use. Typically, a suture is attached to these devices by threading the suture through a hole (i.e., through-threading) and tying a knot to secure the suture. This threading operation is typically very difficult to perform during a surgical operation and may take as long as fifteen minutes to accomplish. Alternatively, in some cases a suture is preattached to the anchor. Nevertheless, if the suture breaks during use the entire anchor may have to be removed in order to reattach a suture. And, removal of these conventional anchors is difficult and traumatic because installation is typically irreversible. That is, once they are inserted into a substrate, they cannot be removed without causing damage to the substrate.

Further, because these devices operate by "digging" into or creating friction with the surrounding substrate, they require a sufficiently thick substrate to effectively anchor. Therefore, although these devices may provide an effective anchor in a relatively thick bone (e.g., the knee, shoulder, elbow, etc.) they are much less effective in areas where the bone is thinner (e.g., craniofacial, metatarsals, metacarpals). Further, these devices may extend well below the surface of the bone, and thus provide a path for suture chafe.

Moreover, problems with difficulty of use extend to conventional bone screws as well. For instance, although a conventional bone screw may be installed and removed, they typically do not provide for attachment of sutures or for secure self-retaining attachment of the screwdriver to the screw. More specifically, if a suture is to be attached to a conventional bone screw, it will typically have to be threaded under the screw head or through a hole that the bone screw has been retrofitted with. Additionally, bone screws are often difficult to install in the operating room. That is, bone screws are generally inserted into predrilled holes, and have to be held in place until the threads of the screw engage with the sides of the predrilled hole. As such, conventional bone screws require pre drilling and a capture device be used in the operating room to form a hole and place a bone screw. Thus, there is a necessity of a capture device in the operating room and an additional sterilization procedure.

Further, the act of holding a bone screw can be difficult when the bone screw is being inserted into a confined area. Although there are some methods of holding a bone screw to the driver these conventional methods of holding the bone screw to the driver are often unsatisfactory. One conventional method involves the use of a clasp structure to hold the bone screw to the driver as shown in FIG. 8a & 8b. While this method may be effective in certain circumstances, the clasp structure is generally cumbersome and obscures the view of the hole and screw making it difficult to start the screw in a bloody environment or confined space. Another conventional method involves using a flared driver blade to establish a friction fit between the driver blade and a slot on the bone screw head as shown in FIG. 9a & 9b. Nevertheless, this configuration has a drawback as well in that the strength of the holding force varies depending on the strength of the force used to establish the friction fit. It is difficult to gauge the strength of the holding force and thus, the hold is often too weak or too strong. If the hold is too weak, the screw may fall off If the hold is too strong, a strong force may be necessary to disengage the screw from the driver. If this force exceeds the force of the holding bone it may strip the screw from its hole or fracture additional bone.

There are also applications in which the use of conventional anchors is inappropriate or in which it is difficult to find a suitable substrate to use for conventional anchors or in which anchor size is inappropriate. For example, during installation of a piece of surgical hardware, such as a cardiac pacemaker or surgical prosthesis there are typically certain locations on the hardware that need to be secured to adjacent structures or where it would be desirable to have a point of attachment. Examples include: optical implants, dental implants or extraction devices, cardiac pacemakers, catheter tubes, drainage tubes, general orthopedic implants, bladder suspensions devices, etc. Nevertheless, there is often no rigid substrate in the vicinity that is suitable for anchoring. Moreover, it is undesirable to have through holes, raised surfaces, or extensions on the surfaces of these devices for both clinical and cosmetic reasons.

Therefore, the inventor has recognized that a need has arisen for new self-retaining mechanical fasteners, such as self-retaining screws, self-retaining bone screws, suture anchors and more particularly a track and a process for fabricating the track into general hardware that overcomes the drawbacks discussed above.

SUMMARY OF THE INVENTION

It is an object of the invention to provide self-retaining mechanical fasteners, such as screws and bone screws and anchors that overcomes the drawbacks of conventional mechanical fasteners, screws, bone screws, anchors, and suture anchors.

It is another object of the invention to provide a self-retaining general fastener.

It is another object of the invention to provide a self-retaining, self-drilling screw.

It is another object of the invention to provide a self-retaining, self-drilling suture anchor.

It is another object of the invention to provide a suture anchor that enables a suture to be attached/secured in a plurality of configurations.

It is another object of the invention to provide a process for fabricating a suture anchor that overcomes the drawbacks of conventional suture anchors.

It is another object of the invention to provide a process for fabricating a self-drilling bone screw or suture anchor that overcomes the drawbacks of conventional self-drilling configurations.

It is another object of the present invention to provide a suture anchor/bone screw that includes a self-retaining component that facilitates installation.

According to one embodiment, a general mechanical fastener is disclosed. The mechanical fastener comprises an elongate member having a first end and a head portion. The first end is adapted for insertion into a substrate. The head portion has at least one surface and comprises means to engage with a driver. The mechanical fastener also includes at least one arm formed within the head portion. The arm has an outer surface integral with an outer surface of the head portion and an inner surface that includes a projection at an end of the arm.

According to another embodiment, a suture anchor is disclosed. The suture anchor comprises an elongate member having a first end and a head portion. The first end is adapted for insertion into a substrate. The head portion has at least one surface and comprises means to engage with a driver. The suture anchor advantageously comprises a track formed within the head portion below the at least one surface. The track is operative to anchor at least one suture without through threading.

According to another embodiment, a device for anchoring at least one suture to surgical hardware is discloses. The surgical hardware has at least one surface located thereon. The device comprises a track formed within the surgical hardware below the surface. The track is used for anchoring at least one suture.

According to another embodiment, a self-retaining screw is disclosed. The self-retaining screw comprises an elongate member having a first end and a head portion. The first end is adapted for insertion into a substrate and the head portion has an upper surface. A means for engaging the screw with a driver is formed within the head portion. And, at least one spring arm is formed within the head portion adjacent the means for engaging. The at least one spring arm provides a locking force between the head portion and the driver and thus makes the screw self-retaining.

According to another embodiment, a process for fabricating a track within a structure is disclosed. The process comprises the step of positioning a structure within which the track is to be fabricated. Once the structure is positioned, an access cut is fabricated approximately perpendicular to a surface of the structure using an electrical discharge machining (EDM) process. Finally, a track is fabricated beneath the surface through the access cut using an EDM process. The access cut and the track form a continuous void within the structure.

According to another embodiment, a process for fabricating a track within a head portion of a plurality of blanks is disclosed. The process comprises the step of providing a fixture for fabrication. The blanks are positioned on the fixture in a matrix. A surface of the head portions of the plurality of blanks is then prepared for fabricating the track. After the surfaces are prepared, at least one track is simultaneously fabricated beneath the prepared surface of the head portion of each blank within a row of the matrix.

According to another embodiment a self-drilling suture anchor is disclosed. The self-drilling suture anchor comprises an elongate member having a first end and a head portion. The first end is adapted for drilling into and securing the elongate member within a substrate. The head portion has at least one surface and comprises means to engage with a driver. An anchoring means is formed within the head portion and is operative to anchor at least one suture without through threading.

According to another embodiment, a self-retaining suture anchor is disclosed. The self-retaining suture anchor comprises an elongate member that has a first end and a head portion. The first end of the elongate member is adapted for insertion into a substrate. The head portion comprises means to engage with a driver and first and second cleat members. The first cleat member is positioned on a first side of the means to engage with a driver. The second cleat member is positioned on a second side of the means to engage with a driver. The first cleat member and the second cleat member are operative to anchor suture. Moreover, at least one of the first cleat member and the second cleat member provides a locking force between the driver and the head portion.

According to another embodiment, an apparatus for preventing suture from releasing from a suture anchor is disclosed. The suture anchor comprises a head portion having at top surface with a means to engage with a driver. The suture anchor also comprises at least one arm, formed within the head portion adjacent the means to engage, that provides a locking force between the head portion and a driver. The apparatus comprises a plug shaped for insertion into the means to engage with a driver. The plug is operative to prevent release of suture positioned below the at least one arm. The locking force is operative to secure the plug within the means to engage.

According to another embodiment, a method of inserting a suture anchor into a substrate is disclosed. The suture anchor comprises an elongate member having a first end adapted for insertion into a substrate, and a head portion that comprises a means to engage with a driver. The method comprises providing a base and screwing the suture anchor into the base. Suture is then anchored to the head portion of the suture anchor and the suture anchor is then removed from the base by unscrewing with a driver. When the suture anchor is removed from the base, the suture winds around the driver. The suture anchor is then screwed into the substrate. When the suture anchor is screwed into the substrate, the suture unwinds from around the driver to position the suture for use.

According to another embodiment, a method of fabricating a self-drilling tip on at least one elongate member is disclosed. The method comprises an initial step of providing a fixture and positioning at least one elongate member within the fixture. Once the elongate member is positioned, an EDM element is positioned proximate to the elongate member to prepare for fabrication. Finally, a self-drilling component is fabricated on the elongate member using said EDM element. The method is useful for a single elongate member or on a plurality of elongate members.

The present invention provides improved general mechanical fasteners such as, screws, bone screws and suture anchors. The general mechanical fastener according to various embodiments of the present invention includes a track and/or a self-retaining component incorporated into the head of a fastener such as a bolt, a screw or a rivet, without interfering with the normal function of the fastener. For example, if the fastener is a screw, the screw may be removed and reinserted as a normal screw is, without damaging substrate. According to various embodiments of the present invention, the track and/or self-retaining component is incorporated in the head of a bone screw without interfering with the bone screw function and therefore the bone screw may be removed and reinserted without damaging the bone. Further, the track and/or self-retaining component can be adapted to any existing screw head configuration, e.g., slot, hex, philips, octagon, star, square, etc. According to other embodiments of the present invention, the track may also be advantageously incorporated into other types of surgical hardware such as, cardiac pace makers and prostheses. The present invention comprises in a particular embodiment, a suture anchor/bone screw that includes a self retaining component that enables single-handed installation and/or a self-drilling component which eliminates predrilling.

The present invention also provides a method for fabricating a suture anchor or general mechanical fastener with or without a self-drilling tip. The method according to various embodiments of the present invention enables the various embodiments of mechanical fastener to be produced singly or in mass in a cost effective manner.

These and other advantageous aspects of the present invention are apparent to one skilled in the art from the following figures, description and claims.

BRIEF DESCRIPTION OF THE DRAWINGS

The features and objects of the present invention, and the manner of attaining them are explained in detail in the following DETAILED DESCRIPTION OF THE INVENTION when taken in conjunction with the accompanying drawings wherein:

FIG. 1b is an enlarged view of portion B of the suture anchor shown in FIG. 1a.

FIG. 1c is a top view of the head portion of the suture anchor shown in FIG. 1a.

FIG. 2b is a top view of the head portion of the self-drilling suture anchor shown in FIG. 2a.

FIG. 2c is another side view of the self-drilling suture anchor shown in FIG. 2a.

FIGS. 4a–4l show various embodiments of suture anchor configurations according to the various embodiments of the present invention.

FIG. 5a is a side view of a bone screw and or suture anchor according to another embodiment of the present invention.

FIG. 5b is an enlarged view of portion B of the suture anchor shown in FIG. 5a.

FIG. 5c is a top view of the head portion of the bone screw shown in FIG. 5a.

FIG. 6 depicts incorporation of the suture anchor track shown in FIG. 5 into a piece of general surgical hardware (a bone plate).

FIGS. 8a and 8b depict an engagement sequence between a conventional driver with a capture device and a conventional bone screw.

FIGS. 9a and 9b depict an engagement sequence between a conventional flared blade driver (self-retaining driver) and a conventional bone screw.

FIG. 10b is an enlarged view of the self-retaining component of the screw shown in FIG. 10a.

FIG. 10c is a top view of the head portion of the self-retaining screw shown in FIG. 10a.

FIGS. 16a–16d depict a fixture used in a process for fabricating a track within an existing structure and/or in a process for fabricating an end portion on a threaded portion of a mechanical fastener according to one embodiment of the present invention.

FIGS. 17a and 17b depict a fixture including a clamping mechanism used in a process for fabricating a track within an existing structure and/or in a process for fabricating an end portion on a threaded portion of a mechanical fastener according to one embodiment of the present invention.

FIG. 22b is a top view of the head portion of the suture anchor shown in FIG. 22a.

FIG. 22c is another side view of the bone screw shown in FIG. 22a.

FIG. 22d is an enlarged view of portion B of the suture anchor shown in FIG. 22a.

FIG. 23b is a top view of a suture anchor having an external cleat shown in FIG. 23a.

FIG. 23c is another side view of a suture anchor having an external cleat shown in FIG. 23a.

FIGS. 29a to 29c depict a manufacturing fixture having collets.

FIGS. 37a, 37b and 37c depict the step of inserting a suture anchor into a base material according to a method of using a suture anchor of the present invention.

DETAILED DESCRIPTION OF THE INVENTION

The preferred embodiment of the present invention and its advantages are best understood by referring to FIGS. 1 through 32 of the drawings, like numerals being used for like and corresponding parts of the various drawings.

The anchor/self-retaining track according to the various embodiments of the present invention comprises a track that is incorporated into an existing structure. In the context of this disclosure, a track is considered a recess, a groove, a channel, an indentation, a hollow, a notch, a trench, a rut, a flute or a furrow configured to anchor a suture within. Examples of structures within which the track may be incorporated include screws, bone screws, plates, surgical plates, surgical prostheses/implants, etc. When incorporated into a bone screw, the track provides a versatile anchor enabling attachment/securement of suture in multiple configurations without interfering with the function of the bone screw and/or a self-retaining component to facilitate installation. Both the self-retaining and suture anchoring functions are explained in more detail below.

Figure 1A:
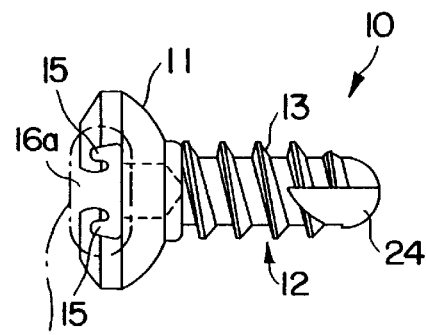
FIG. 1a is a side view of a suture anchor according to a preferred embodiment of the present invention.
Figure 1B:
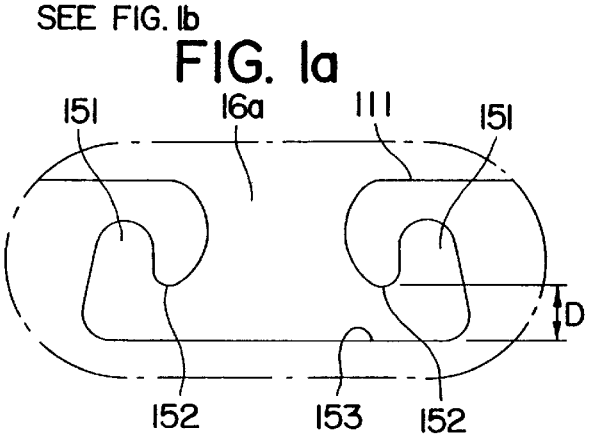
Figure 1C:
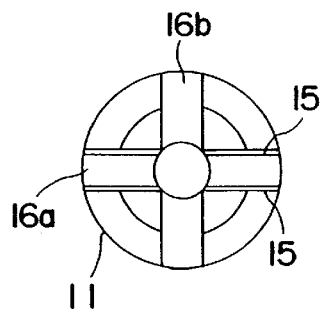

A preferred embodiment of the present invention is shown in FIGS. 1a–1c. FIG. 1a is a side view of a bone screw 10. Bone screw 10 includes head portion 11 and elongated portion 12. Elongated portion 12 includes threads 13 and self-tapping portion 14. As is known, threads 13 provide a means for engaging bone screw 10 with a substrate. Self-tapping portion 14 enables bone screw 10 to be used without separately tapping the hole within which it is to be used. In an alternative embodiment, bone screw 10 may have any thread configuration suitable for use within the human body including for example, modified buttress, and self-drilling.

The suture anchor track according to this preferred embodiment of the invention is incorporated within head portion 11 of bone screw 10. As can be seen from FIGS. 1a and 1c, head portion 11 includes suture anchor tracks 15 and transverse slots 16a and 16b. Transverse slots 16a and 16b are provided to engage bone screw 10 with a screw driver. Suture anchor tracks 15 provide an area within which a suture may be retained and thus anchored. The structure and operation of suture anchor tracks 15 is explained in conjunction with FIG. 1b which is an enlarged view of portion B of bone screw 10 shown in FIG. 1a.

As can be seen from FIGS. 1b and 1c, in a preferred embodiment, suture anchor tracks 15 are fabricated along one of transverse slots 16. When any bone screw engages with a screw driver, a driving force (in the form of a torque) is imparted to the bone screw by the screw driver through an engaging means in the head of the screw. In the case of screw 10, the engaging means comprises transverse slots 16a and 16b. Nevertheless, in order to protect suture anchor tracks 15 from deformation caused by the screw driver and the torque transferred to screw 10 by a screw driver, transverse slots 16a and 16b are fabricated so that slot 16b absorbs a greater proportion of the torque. This is accomplished by providing a rigid support in one of the transverse slots and tolerancing the self-retaining track such that a calculated bending moment is achieved.

As shown in FIG. 1b, suture anchor tracks 15 are formed on either side of one of transverse slots 16A and comprise a cavity 151 beneath the top surface 111 of head portion 11 of bone screw 10. Suture anchor tracks 15 include retaining arms 152 that demarcate cavity 151 and the opening to cavity 151. In operation, to anchor a suture, the suture is slipped into slot 16 and through the opening between the tip of retaining arm 152 and the lower most surface 153 of cavity 151. The width D of the opening between the tip of retaining arm 152 and the lower most surface 153 of cavity 151 is carefully toleranced to be slightly smaller than the diameter of the suture to be used. Thus, once the suture passes under the tip of retaining arm 152 it will not easily pass out of cavity 151. In a specific embodiment, the width D is about 0.008 inches. This embodiment is sized for use with 3-0 diameter suture but will also work with smaller and larger diameter suture. Further, because the suture is typically being worked with at an elevation above head portion 11, the suture will not accidentally come out of suture anchor 15. Moreover, the track is configured such that a direct downward force is required to dislodge suture or related material. That is, a particular sequence of motions are necessary to remove a suture from suture anchor track 15. Specifically, in order to remove a suture from suture anchor track 15 without breaking the suture or feeding through, the suture is pulled down into surface 153 and toward slot 16 from where it can be removed.

Once inside cavity 151, the suture may be anchored in a number of ways. For example, a knot of sufficient diameter may be formed on one end of the suture and then the suture pulled through cavity 151 until it reaches the side of head portion 11 where it reaches an impasse. Alternatively, the suture may be knotted around head portion 11. An infinite number of variations are possible.

Figure 22A:
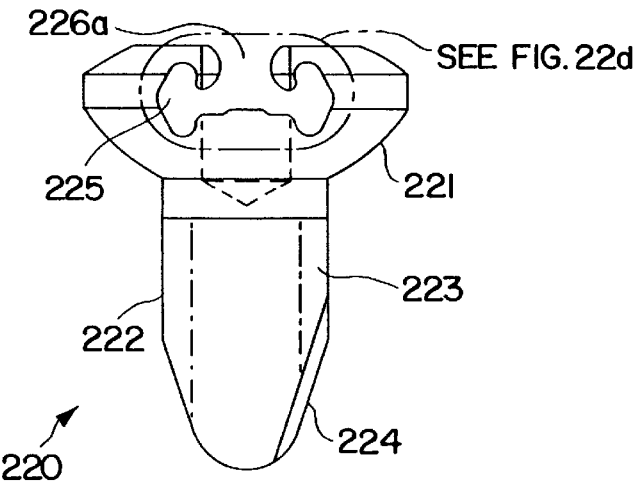
FIG. 22a is a side view of a suture anchor according to a preferred embodiment of the present invention.
Figure 22B:
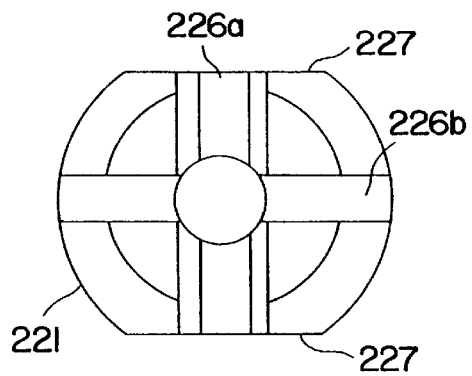
Figure 22C:
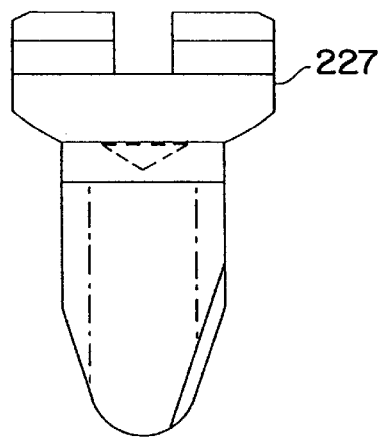
Figure 22D:
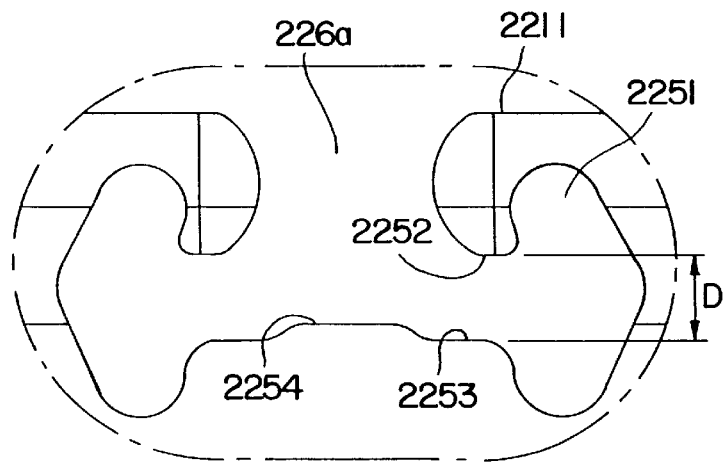

Another embodiment of suture anchor is depicted in FIGS. 22a to 22c. The embodiment of FIGS. 22 differs from the embodiment of FIGS. 1 in two primary ways. In the embodiment of FIGS. 22, head portion 221 is configured to include opposite beveled surfaces 227 (best seen in FIGS. 22b and 22c). Beveled surfaces 227 improve suture failure strength by squaring the path of the suture on the outside of tracks 225 and thus reducing the possibility of pinching suture between substrate and head portion 221. Moreover, head portion 221 also includes stop plate 2254 (seen best in FIG. 22d) to control engagement depth. Stop plate 2254 is contoured to direct suture into tracks 225 and also provides an obstruction to suture exiting the track accidentally. The function of tracks 225 in FIGS. 22 is otherwise similar to tracks 15 explained in conjunction with FIGS. 1.

Figure 2A:
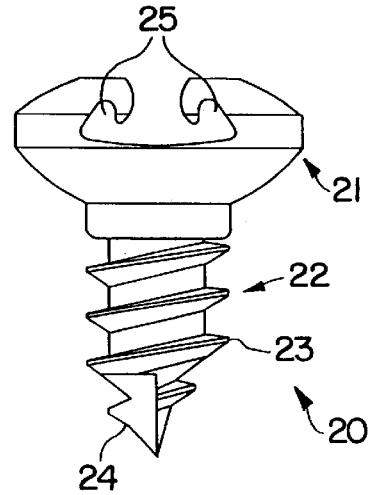
FIG. 2a is a side view of a self-drilling suture anchor according to a another embodiment of the present invention.
Figure 2B:
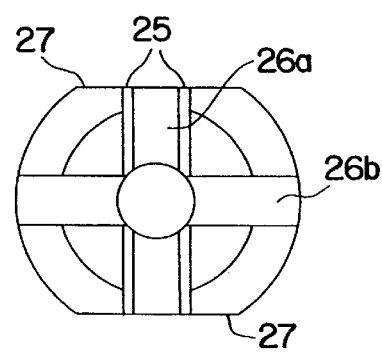
Figure 2C:
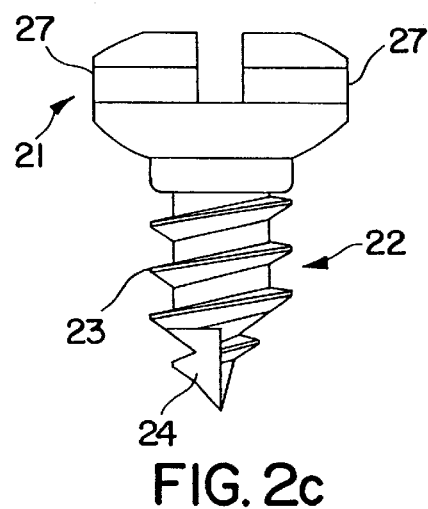

In another embodiment, one or more suture anchor tracks 15 are incorporated into the head of a self-drilling bone screw. A self-drilling suture anchor 20 is shown in FIGS. 2a to 2c. Self-drilling suture anchor 20 comprises head portion 21 and elongated portion 22. According to this embodiment, elongated portion 22 includes threads 23 and self-drilling portion 24. As is known, threads 23 provide a means for engaging self-drilling suture anchor 20 with a substrate. Self-drilling portion 24 enables suture anchor 20 to be used without separately boring a hole within which it is to be used. As stated above, this is advantageous in that it saves time during an operation and reduces the amount of equipment needed to be prepared for and used during an operation.

Figure 42:
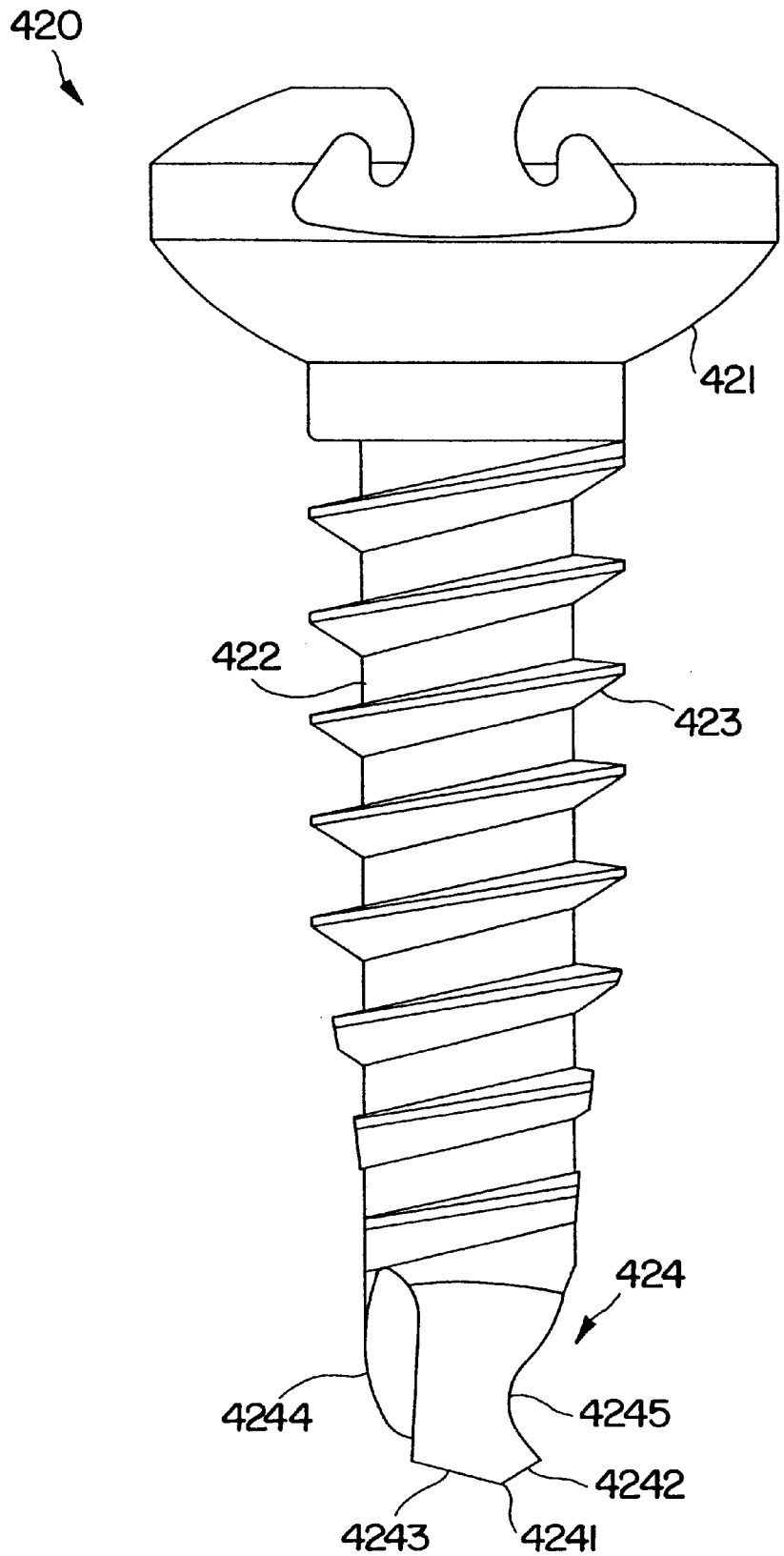
FIG. 42 depicts a self-drilling suture anchor (or bone screw) according to a preferred embodiment of the present invention.

A preferred configuration of self-drilling suture anchor is shown in FIG. 42. Self-drilling suture anchor 420 comprises head portion 421 and elongated portion 422. According to this embodiment, elongated portion 422 includes threads 423 and precision self-drilling portion 424. As is known, threads 423 provide a means for engaging self-drilling suture anchor 420 with a substrate. Precision self-drilling portion 424 enables suture anchor 420 to be used without separately boring a hole within which it is to be used. Additionally, precision self-drilling portion 424 has a shape and configuration similar to that of a conventional drill bit and comprises point 4241, and edges 4242, 4243, 4244, 4245. Point 4241, edge 4242 and edge 4243 provide vertical boring while edges 4244 and 4245 provide lateral cutting and transport cut material. In a preferred embodiment, each of point 4241 and edges 4242 to 4245 are fabricated using an EDM process as explained below.

Figures 43E, 43F, 43G, 43H:
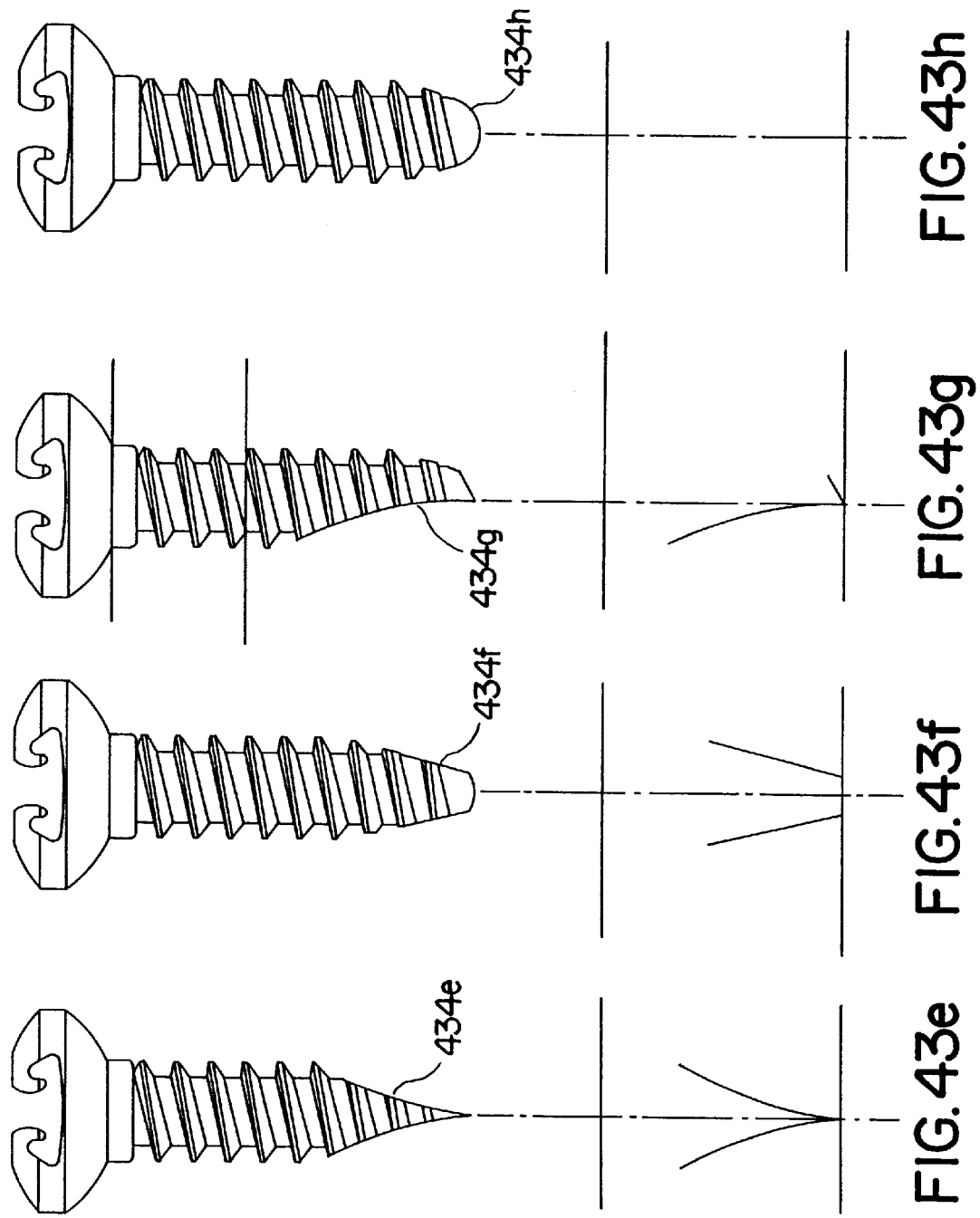
FIG. 43 depicts several alternative configurations for a self-drilling component according to another embodiment of the present invention.

FIG. 43 depicts additional configurations possible for a self-drilling component of a self-drilling suture anchor or bone screw. Two of the various configurations shown in FIG. 43 can be combined into a single self-drilling head portion as well as used singly. That is, each of FIGS. 43a–43h represents a side view of a self-drilling component. A self-drilling tip could be constructed that has two different self-drilling components. For instance, a self-drilling tip could be constructed having the self-drilling component of FIG. 43a and the self-drilling component of FIG. 43b when viewed from a position rotated by 90 degrees. Similarly, a self-drilling tip could be constructed having a self-drilling component of FIG. 43c and a self-drilling component of FIG. 43f Fabrication of such self-drilling tips is discussed in more detail below.

Head portion 21 of self-drilling suture anchor 20 comprises suture anchor tracks 25 and transverse slots 26a and 26b. Transverse slots 26a and 26b are provided to engage self-drilling suture anchor 20 with a screw driver. Suture anchor tracks 25 provide an area within which a suture may be retained and thus anchored. The structure and operation of suture anchor tracks 25 is substantially the same as the structure and operation of suture anchor tracks 15 explained in conjunction with FIG. 1 and will thus not be described again.

In a preferred embodiment, the suture anchors discussed above are fabricated from a material that has been approved by the FDA for use within the human body and that is sufficiently hard to withstand particular fabrication processes, such as the EDM and wire EDM processes described in detail below. In one embodiment, the above-described suture anchors are composed of a low-carbon, corrosion-resistant, body-grade metal (either non-magnetic or magnetic). In a preferred embodiment the suture anchors are comprised of Titanium. In other embodiments, the suture anchors are composed of stainless steel, cobalt chrome, brass or aluminum. In another embodiment, the above-described suture anchors are composed of a reabsorbable biocompatible material such as polyglycolic acid or polylactic acid. In still another embodiment the above-described suture anchors are composed of various non-metallic materials such as ceramics, carbon fiber/composites or plastics.

Suture anchors including self-drilling portions may be manufactured according to various manufacturing processes. In a preferred embodiment, the suture anchors including self-drilling suture anchors are manufactured using a wire EDM process. This manufacturing is explained in detail below.

Figure 3A:
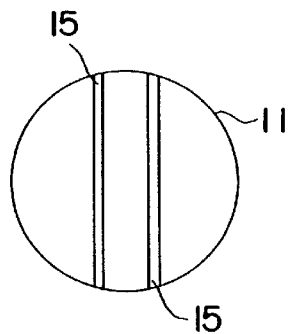
FIG. 3a shows the head portion of a screw having a slot configuration and including a suture anchor track according to one embodiment of the present invention.
Figure 3B:
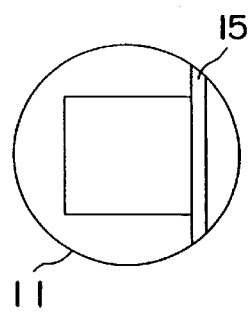
FIG. 3b shows the head portion of a screw having a square cutout configuration and including a suture anchor track according to one embodiment of the present invention.
Figure 3C:
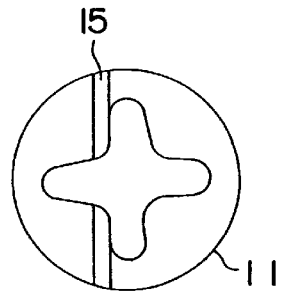
FIG. 3c shows the head portion of a screw having a Philips configuration and including a suture anchor track according to one embodiment of the present invention.
Figure 18B:
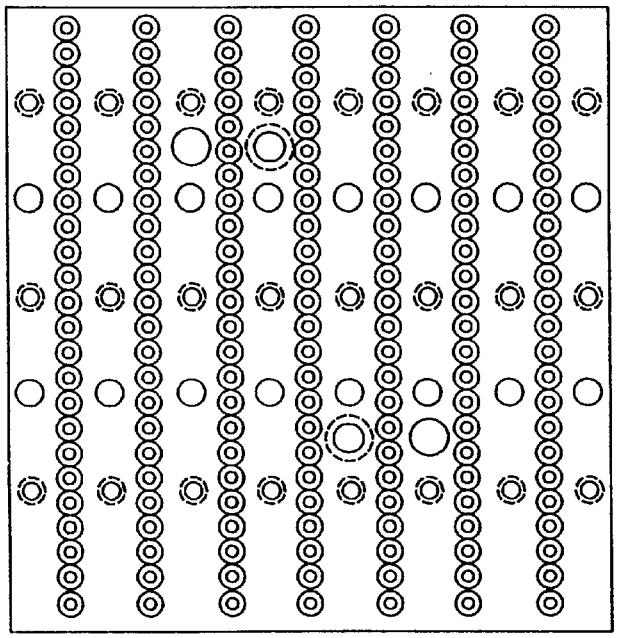
FIGS. 18a and 18b depict a fixture including an encapsulated dowel used in a process for fabricating a track within an existing structure and/or in a process for fabricating an end portion on a threaded portion of a mechanical fastener according to one embodiment of the present invention.
Figures 2, 18A:
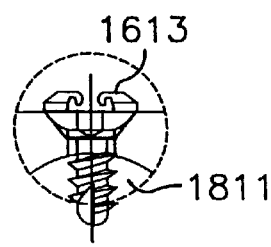
Figures 1, 18A:
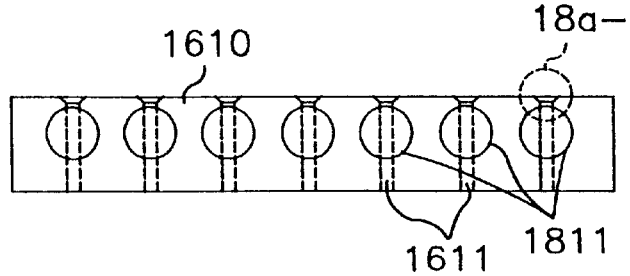

A suture anchor track according to the various embodiments of the present invention is not limited to the specific configurations shown in FIGS. 1, 2 and 22. For example, a suture anchor track according to the present invention may be used with means of engaging a screw driver other than transverse slots shown in FIG. 1. FIG. 3 show cross-sections across the top of head portions of screws and indicates incorporation of the suture anchor track into other configurations for engagement such as, a single slot (FIG. 3a), a square shaped cutout (FIG. 3b), and a Philips cutout (FIG. 3c), etc. Other configurations are possible and are within the scope of the embodiments of the present invention. Suture anchor track 15 may be incorporated into any of these head configurations by cutting a slot through the head portion, for example, along one side of the square cutout used in a screw designed to be driven by a square headed screw driver.

Further, a suture anchor track according to the embodiments of the present invention may take other configurations. FIGS. 4a–4f show various embodiments of suture anchor track configurations according to the various embodiments of the present invention. FIGS. 4a–4f depict side views of bone screws 40 having head portions 41 and elongated portions 42. According to the various embodiments shown in FIGS. 4a–4f, elongated portions 42 include threads 43 and self-tapping portions 44. Elongated portions 42 may also be provided with a self-drilling portion.

Head portions 41 of suture anchors 40 have suture anchor tracks 45a and at least one slot 46 fabricated therein in different configurations. Slots 46 are provided to engage suture anchor 40 with a screw driver. Other configurations may be used to engage suture anchors 40 with a screw driver. Suture anchor tracks 45 provide an area within which a suture may be retained and thus anchored.

Although the structure of each of suture anchor tracks 45 depicted in FIGS. 4 is somewhat modified, their operation is similar to the suture anchor tracks explained above in conjunction with FIGS. 1, 2 and 22. FIGS. 4a and 4b depict a spiral suture anchor track 45a. In operation, the spiral shape of suture anchor track 45a helps ensure that a suture does not slip out of the track. Moreover, the spiral shape enables a number of sutures to be anchored/secured within the suture anchor track 45a.

Figure 4A:
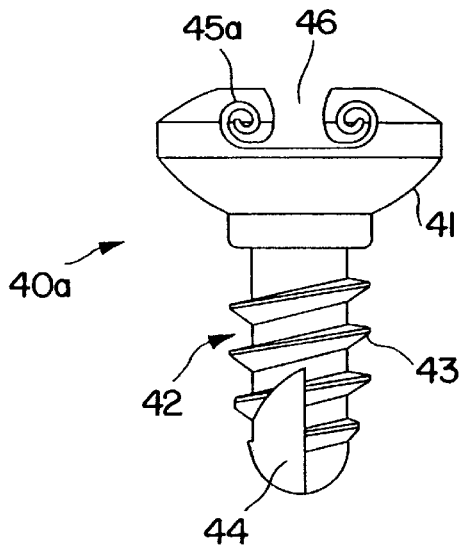
Figure 4C:
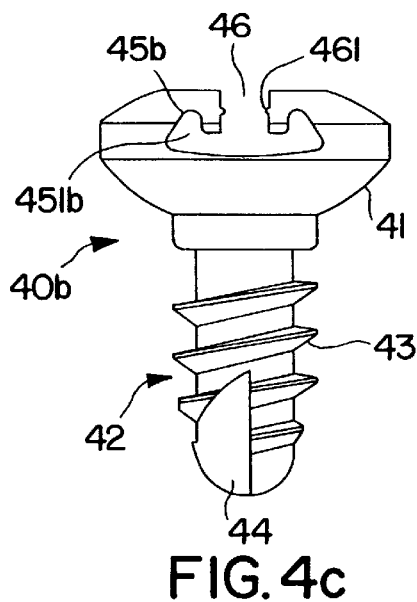
Figure 4B:
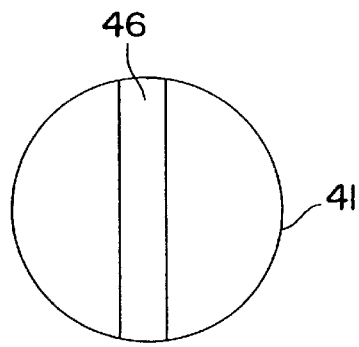
Figure 4D:
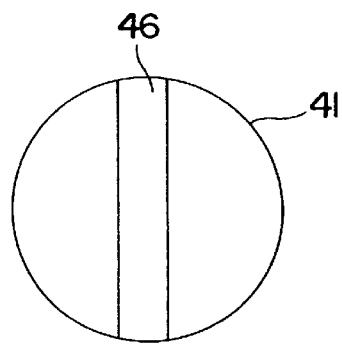

FIGS. 4c and 4d depict a suture anchor track 45b having an enlarged cavity 451b. Operation of suture anchor track 45b is similar to that of suture anchor tracks 15 and 25 explained in conjunction with FIGS. 1 and 2 above and thus will not be explained in detail. Note, however, enlarged cavity 451b of suture anchor track 45b enables a number of sutures to be anchored/secured within suture anchor track 45b. Further, slot 46 of suture anchor 40 shown in FIG. 4b comprises gripping members 461 on its inside surfaces. Gripping members 461 are used to help establish an engagement force between suture anchor 40b and a driver used to drive suture anchor 40b.

FIGS. 4e and 4f depict a suture anchor track 45c fabricated beneath an underside surface of head portion 41. Operation of suture anchor track 45c is similar to that of suture anchor tracks 15 and 25 explained above. That is, in order to anchor a suture within suture anchor track 45c, the suture is slipped up over retaining arm 452 and into cavity 451. This operation is typically accomplished before suture anchor 40 is screwed into a substrate. Thus, once suture anchor 40 is secured within a substrate, the suture is locked within track 45c. This configuration of suture anchor is typically used for applications in which an exposed screw head is acceptable. For example, the suture anchor of FIG. 4c may be used in conjunction with a surgical plate.

FIGS. 4g and 4h depict a suture anchor track 45d fabricated within head portion 41 of suture anchor 40d. Operation of suture anchor track 45d is similar to that of suture anchor tracks 15 and 25 explained above. Briefly, a suture is anchored/secured within suture anchor track 45d by slipping the suture under retaining arm 452 and into cavity 451 of track 45d. Once inside track 45d the suture is only removed by going through the particular sequence of motions described in conjunction with FIG. 1. That is, the suture first must be slipped down to the bottom of track 45d to the surface 453. Once the suture is at the surface 453 it may then be slid underneath retaining arm 452.

FIGS. 4i and 4j depict a suture anchor track 45e fabricated around a periphery of head portion 41 of suture anchor 40. With an annular track such as track 45e, a point of access is used in order to gain access to the ends of the suture and so that track 45e serves as a pivot point for the suture. In the embodiment shown in FIG. 4i and 4j, the annular track is interrupted at points 454 which are aligned with slot 46 in order to access the suture. In order to anchor a suture within track 45e, the suture is slipped under retaining arm 452 and into cavity 451 of track 45e. As shown in FIG. 4j, port 454 formed in track 45e at two or more points along the periphery enable the suture end to be accessed and the track used as a pivot point for the suture.

FIGS. 4k and 4l depict a suture anchor track 45f fabricated within head portion 4l of suture anchor 40f. Suture anchor track 45f is slightly different than the previous embodiments in that suture is positioned and captured by bending retaining arms 452 in the direction of the arrows in FIG. 4k. This bending occurs when a screwdriver is engaged in slot 46. After bending, retaining arms 452 prevent the suture from slipping out.

Yet another embodiment of suture anchor is shown in FIGS. 5a–5c. FIG. 5a is a side view of a bone screw 50. Bone screw 50 includes head portion 51 and elongated portion 52. Elongated portion 52 may include threads, self-drilling, and self-tapping portion (not shown) as indicated in FIG. 1.

The suture anchor track according to this preferred embodiment of the invention is incorporated within head portion 51 and around the periphery of head portion 51 thereby giving maximum flexibility for the securing/anchoring of a suture. As can be seen from FIGS. 5a and 5c, head portion 51 includes internal suture anchor track 55a and peripheral suture anchor track 55b and transverse slots 56a and 56b. Transverse slots 56a and 56b are provided to engage bone screw 50 with a screw driver. Suture anchor tracks 55a and 55b provide areas within which a suture may be retained and thus anchored. As can be seen from FIGS. 5b and 5c, and in contrast to the suture anchor shown in FIGS. 1, in this embodiment, suture anchor tracks 55a are fabricated along both transverse slots 56a and 56b.

A suture may be anchored/secured using suture anchor 50 shown in FIGS. 5a–c in a number of configurations. For example, in an operation similar to that described in conjunction with FIGS. 1, to anchor a suture, the suture is slipped into one of slots 56 and slid into cavity 551. Alternatively, a suture may be slid into cavity 551 and then around the periphery of head portion 51 through track 55b and secured by knotting.

Figure 23A:
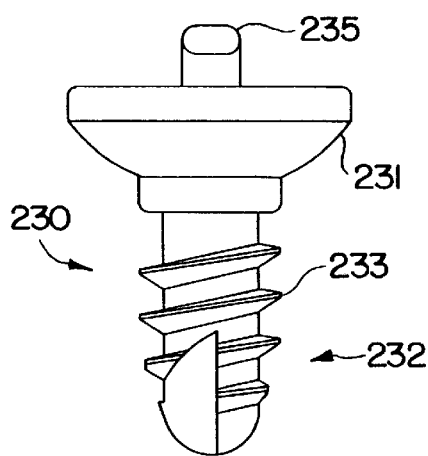
FIG. 23a is side view of a suture anchor having an external cleat according to one embodiment of the present invention.
Figure 23B:
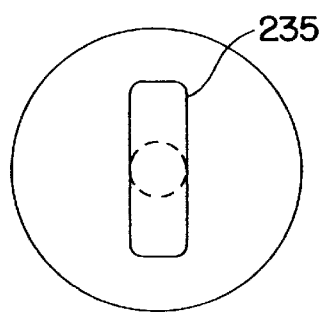
Figure 23C:
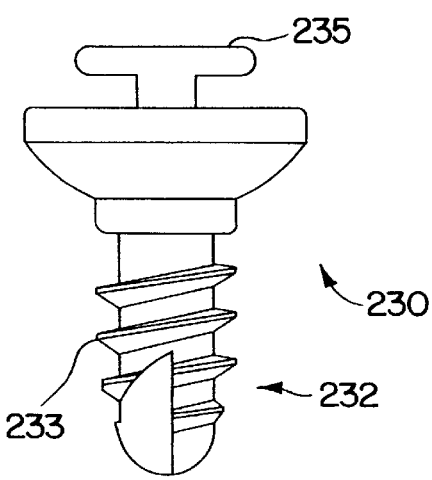
Figure 24A:
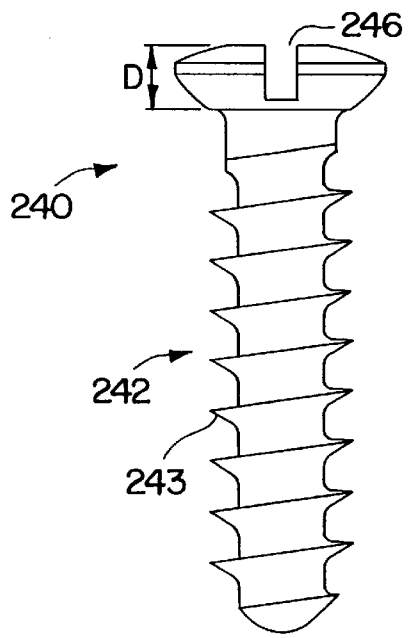
FIGS. 24a and 24b are side views of a low profile suture anchor according to another embodiment of the present invention.
Figure 24B:
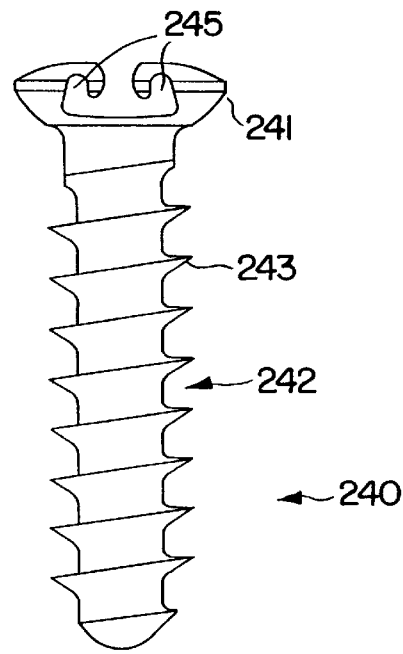
Figures 25A, 25B:
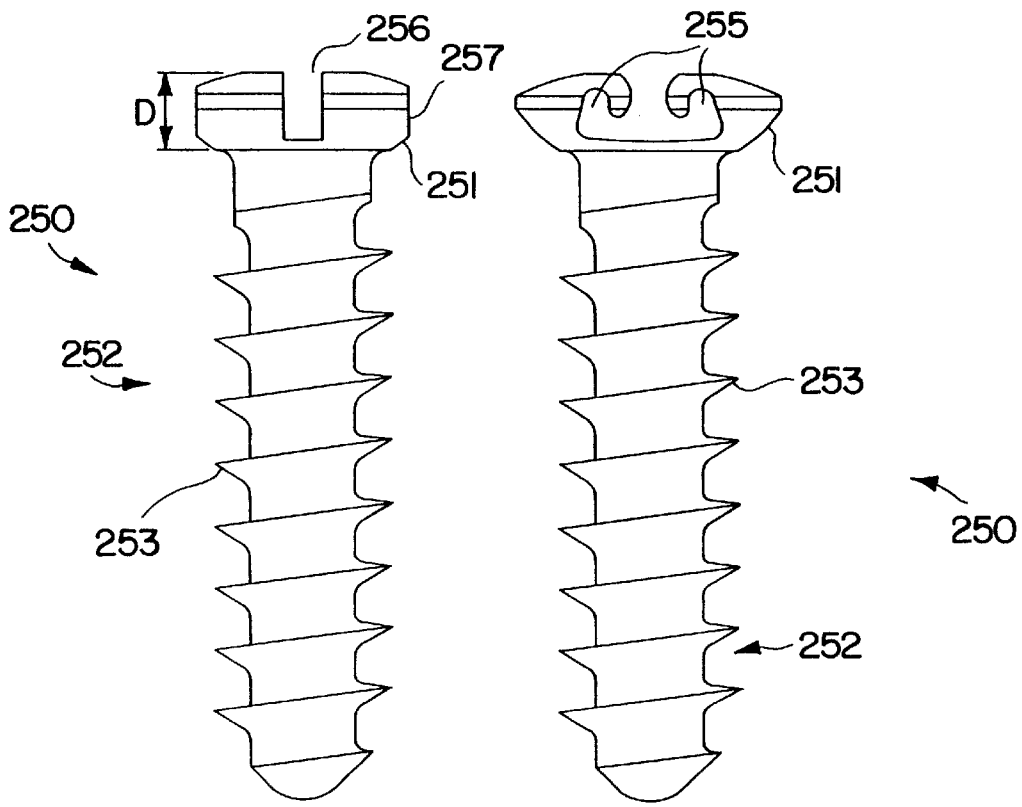
FIGS. 25a and 25b are side views of a low profile suture anchor having a flat side according to another embodiment of the present invention.

According to another embodiment, a suture anchor including an external cleat is shown in FIGS. 23a to 23c. Suture anchor 230 includes external cleat 235 that may be used much like a boat cleat to anchor suture. For example, suture may be knotted around external cleat 235 and thus anchored to suture anchor 230. Suture anchor 230 is inserted and removed using a modified driver similar to a standard driver modified to have an internal cutout matching the shape of the external cleat 235.

FIGS. 24a, 24b, 25a and 25c depict suture anchors having a low head profile. The embodiment of FIGS. 24 includes round head portion 241 and the embodiment of FIGS. 25 includes head portion 251 having beveled surfaces 257. Both suture anchors 240 and 250 shown in FIGS. 24 and 25 have head portions 241 and 251 respectively, that have a low profile, i.e., the depth of their head, D, is reduced as compared to suture anchor 10 shown in FIG. 1, for example. The lower head profile is advantageous because it reduces the possibility that suture anchor 240 or 250 may be visible through the skin as a lump or palpated by the patent. The structure and function of suture anchors 240 and 250 is otherwise similar to the suture anchors explained above.

Figure 30A:
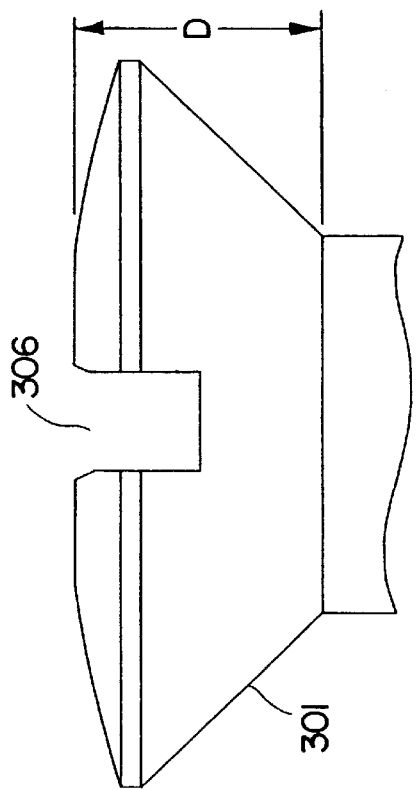
FIGS. 30a and 30b are side views of a suture anchor having enhanced suture retention capabilities in a low profile head according to another embodiment of the present invention.
Figure 30B:
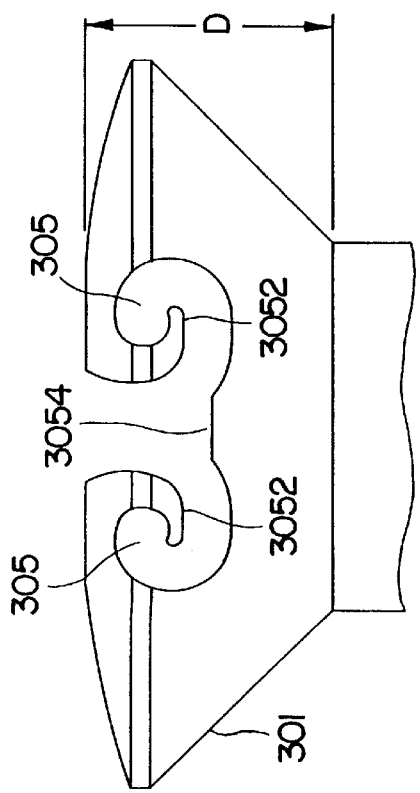

FIG. 30 depicts an embodiment of suture anchor having a low head profile and having a modified track structure. The suture anchor shown in FIGS. 30 includes modified tracks 305 that include extended retaining arms 3052 and stop plate 3054. Extended retaining arms 3052 help prevent suture fallout. Stop plate 3054, as explained above in conjunction with FIGS. 22, helps to control engagement depth of the driver used to insert the suture anchor of FIGS. 30 into a patient. Otherwise, the function of this embodiment of suture anchor is similar to the suture anchors explained above.

Figures 26A, 26B:
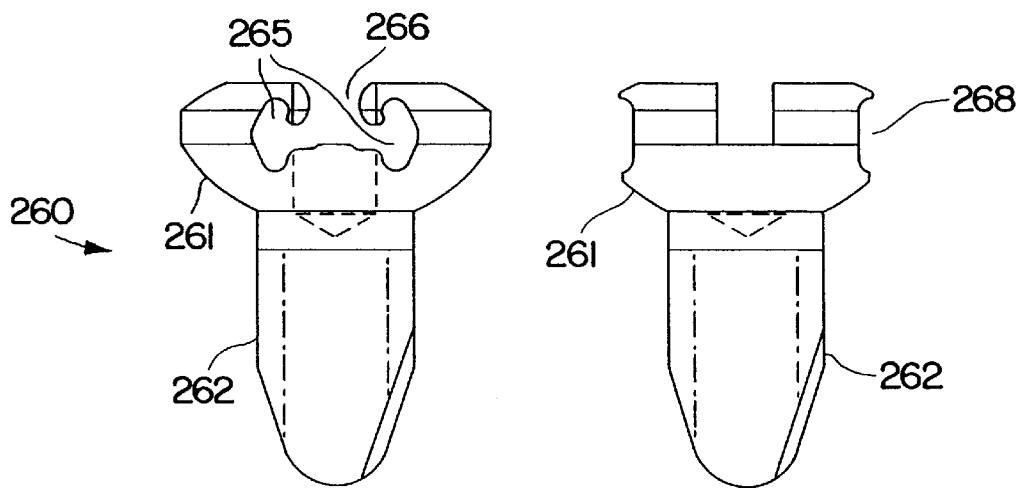
FIGS. 26a and 26b are side views of a suture anchor having a machined radius according to another embodiment of the present invention.

FIGS. 26 depict a suture anchor having a machined radius according to another embodiment of the present invention. In addition to tracks 265, suture anchor 260 shown in FIG. 26b includes head portion 261 having a machined radius 268. Machined radius 268 provides a smooth surface that may be used advantageously to anchor suture around the periphery of head portion 261. Moreover, machined radius 268 helps ensure that head portion 261 does not have any rough surfaces around its periphery that may cause suture to break. The structure and function of suture anchor 260 is otherwise similar to the suture anchors explained above.

Figures 27A, 27B:
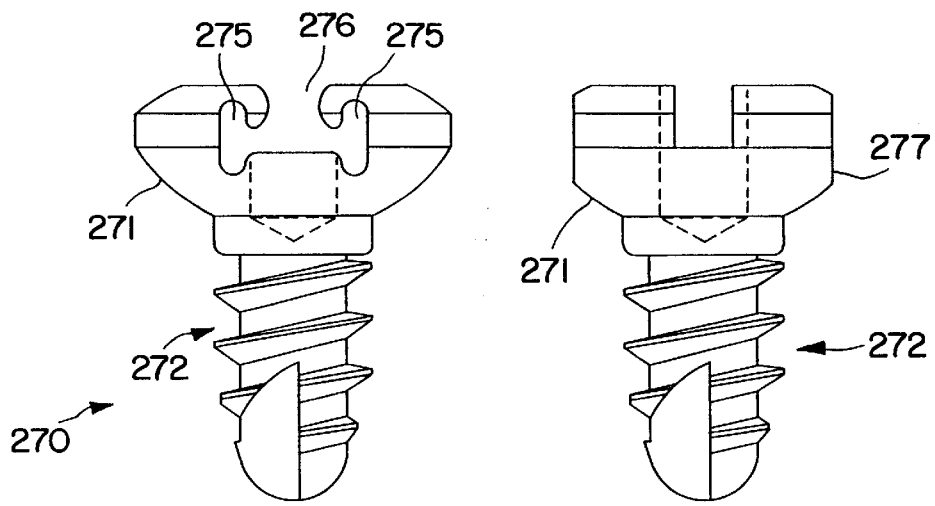
FIGS. 27a and 27b are side views of a suture anchor having a dog-bone track according to another embodiment of the present invention.

FIGS. 27 depict a suture anchor having a modified track structure according to another embodiment of the present invention. As can be seen in FIG. 27a, suture anchor 270 includes head portion 271 having tracks 275 formed therein on opposite sides of slot 276. Opposing tracks 275 have a "dog-bone" configuration but are otherwise functionally similar to the suture anchors explained above.

Figures 28A, 28B:
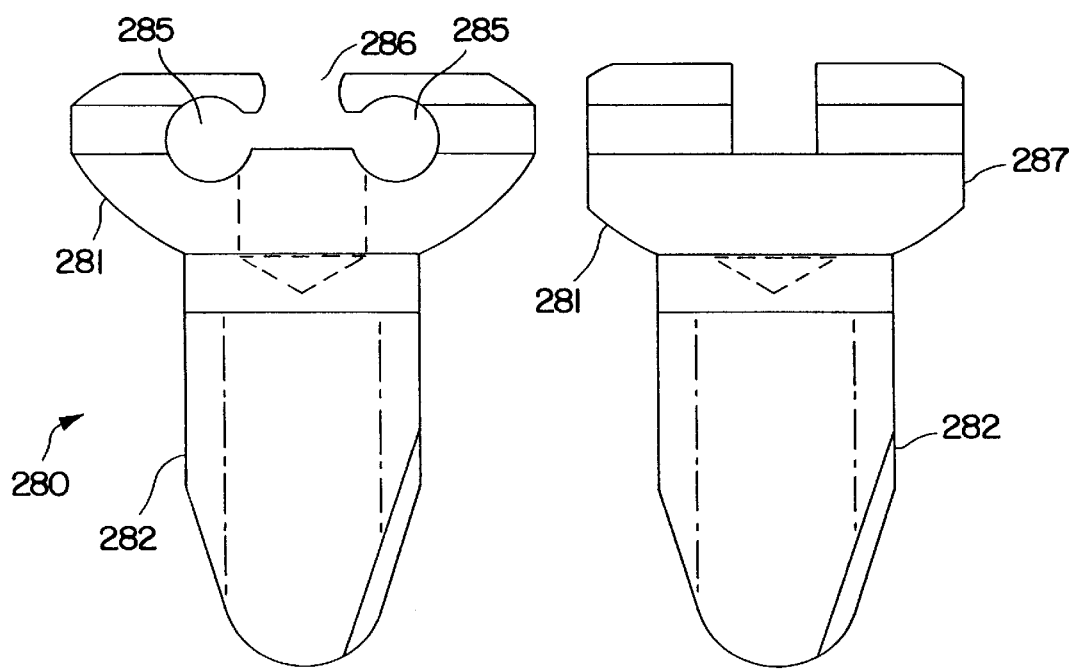
FIGS. 28a and 28b are side views of a suture anchor having a loop track according to another embodiment of the present invention.

FIGS. 28 depict a suture anchor having another modified track structure according to another embodiment of the present invention. As can be seen in FIG. 28a, suture anchor 280 includes head portion 281 having tracks 285 formed therein on opposite sides of slot 286. Opposing tracks 285 have a loop configuration but are otherwise functionally similar to the suture anchors explained above.

Figure 31A:
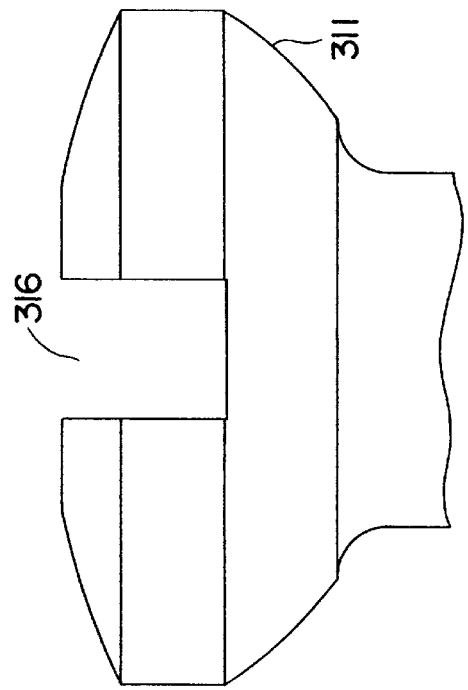
FIGS. 31a and 31b are side views of a suture anchor having a enhanced suture retention capabilities according to another embodiment of the present invention.
Figure 31B:
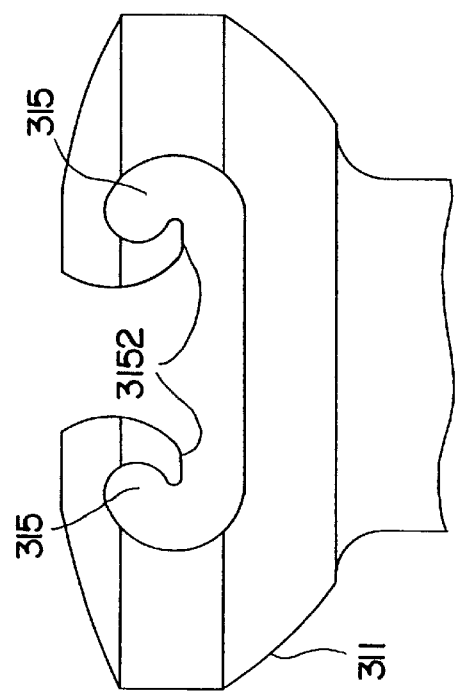

FIGS. 31 depict a suture anchor having another modified track structure according to another embodiment of the present invention. The suture anchor shown in FIGS. 31 includes modified tracks 315 that include extended retaining arms 3152. Extended retaining arms 3152 help prevent suture fallout. Otherwise, the function of this embodiment of suture anchor is similar to the suture anchors explained above.

A suture anchor according to the various embodiments of the present invention may also be incorporated into existing hardware such a surgical plate, an implant, a prosthesis, etc. FIG. 6 shows the incorporation of a suture anchor track 65 according to the present invention into a piece of hardware 60. In one embodiment, suture anchor track 65 is fabricated beneath the surface of a piece of general surgical hardware.

Suture anchor track shown in FIG. 6 is similar to the suture anchor track shown in FIG. 5 and FIG. 1. Nevertheless, any of the configurations of suture anchor discussed above could also be retrofit on the surface of a piece of hardware 60.

Figure 7A:
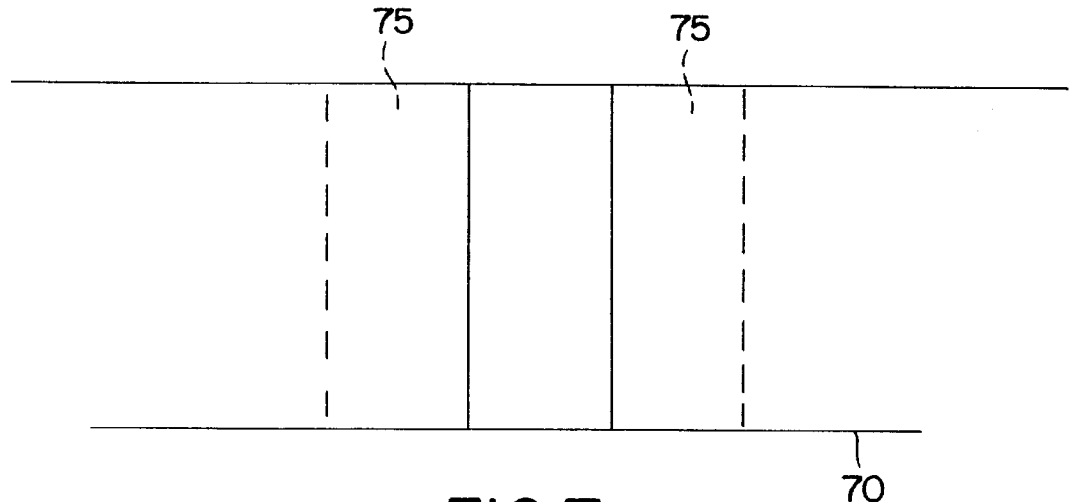
FIGS. 7a and 7b depicts incorporation of the suture anchor track shown in FIG. 1 into a piece of general surgical hardware.
Figure 7B:
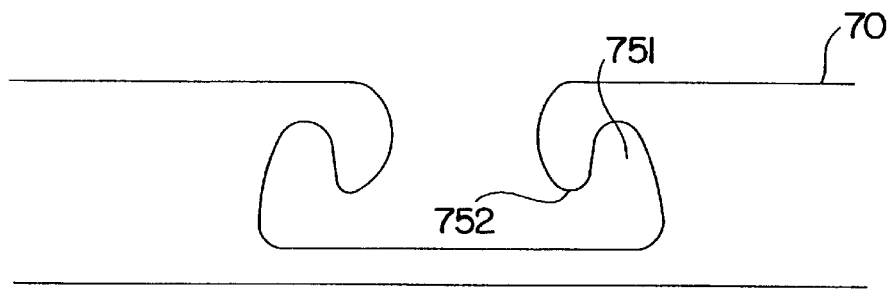

Alternatively, a suture anchor track according to the present invention may also be incorporated into existing hardware without the need for a raised portion on the hardware. FIG. 7 shows the incorporation of a suture anchor track 75 such as is depicted in FIG. 1 into a piece of hardware 70. Suture anchor track 75 comprises retaining arm 752 and internal cavity 751 and operates just as suture anchor track 15 shown in FIG. 1 therefore a description of its operation will not be reiterated here. Such a suture anchor track could be retrofit into any surgical hardware such as a surgical plate, a surgical implant (such as a pace maker) or a surgical prosthesis (such as a hip replacement), etc..

In another embodiment, the present invention provides a self-retaining bone screw. Conventional bone screws are generally driven in using one of various types of driver. FIGS. 8a and 8b show an engagement sequence between a conventional driver 81 and conventional bone screw 80. Referring to FIGS. 8, a conventional driver 81 provides blades 82 having a constant thickness for insertion into the head of a conventional screw 80. Conventional driver 81 will not hold conventional screw 80 to its blades 82. This is disadvantageous because, as explained in the background, when conventional bone screw 80 is initially inserted into a hole it must be held in place. As shown in FIGS. 8, a conventional driver generally must be fitted with a external mechanism 83 that holds conventional screw 80 to blades 82 while the screw is being driven. As stated in the background, this is disadvantageous in that external mechanism 83 is generally cumbersome and obscures the view of the hole and screw making it difficult to start the screw in the operating room environment.

Alternatively, and as shown in FIGS. 9, a modified conventional driver 91 is sometimes used. FIGS. 9a and 9b show an engagement sequence between modified conventional driver 91 and conventional bone screw 90. Modified conventional driver 91 is provided with a blade or blades 92 having a tapered thickness for insertion into the head of a conventional screw 90. Modified conventional driver 91 holds conventional screw 90 to its blade 92 using a conventional friction fit. That is, blade 92 is inserted into the head of conventional screw 90 essentially by forcing tapered blade 92 into the slot in the head portion of conventional screw 90. The greater the force used to push blade 92 into the slot, the greater the friction force holding conventional screw 90 to blade 92. This is disadvantageous because of its imprecision. That is, if too great a force is used to push blade 92 into the slot, then driver 91 may actually be difficult to remove from conventional screw 90 after insertion. This could lead to damage to the bone when attempting to disengage blade 92 from screw 90. In contrast, if too weak a force is used to push blade 92 into the slot, then conventional screw 90 might prematurely disengage from driver 91.

FIG. 10 shows a self-retaining bone screw 100 according to another embodiment of the present invention. Self-retaining bone screw 100 includes head portion 101 and elongated portion 102. Elongated portion 102 includes threads 103 and self-tapping portion 104. As is known, threads 103 provide a means for engaging self-retaining bone screw 100 with a substrate. Self-tapping portion 104 enables self-retaining bone screw 100 to be used without separately tapping the hole within which it is to be used. In an alternative embodiment, self-retaining bone screw 10 may have any thread configuration suitable for use within the human body, e.g., self-tapping.

Self-retaining bone screw 100 according to this embodiment of the invention includes self-retaining component 105 incorporated within head portion 101 of bone screw 100. As can be seen from FIGS. 10a and 10c, head portion 11 includes transverse slots 106a and 106b. Self-retaining component 105 is positioned in general alignment with slot 106a.

Figure 10A:
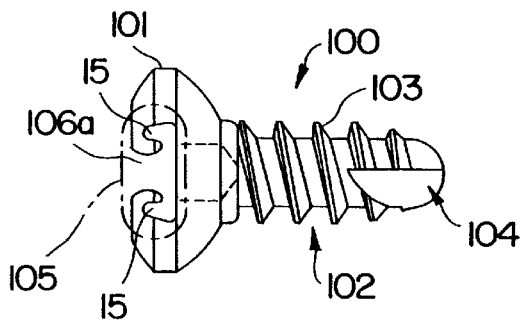
FIG. 10a is a side view of a self-retaining screw according to a preferred embodiment of the present invention.
Figure 10B:
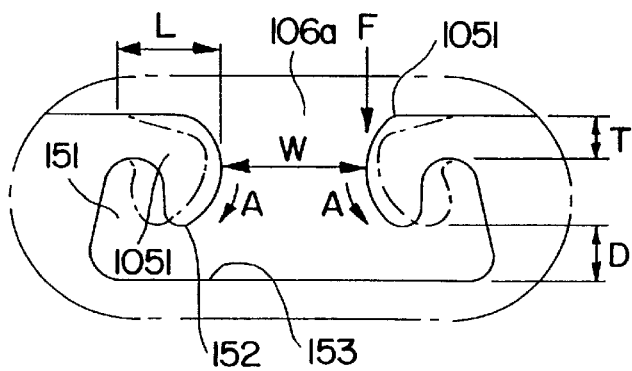

FIG. 10b shows an exploded view of self-retaining component 105. As shown in FIG. 10b, self-retaining component 105 includes cantilever spring arms 1051 that provide a locking force between the head of self-retaining screw 100 and a driver used for inserting screw 100. Such a fit is advantageous because it allows self-retaining screw 120 to be inserted in a single-handed operation. That is, self-retaining screw 100 does not need to be held in place until the threads catch. Rather, screw 100 is held firmly to the driver until the threads catch. The locking force is established as follows. When a conventional driver is inserted into head portion 101 of self-retaining screw 100, the driver applies a force to cantilever spring arms 1051 causing a mechanical stress within spring arms 1051 and causing spring arms 1051 to bend inward from their unstressed state. The stressed state of spring arms 1051 is shown using dashed lines in FIG. 10b. More specifically, when a driver is inserted into the head of screw 100, spring arms 1051 simultaneously bend inwardly. The amount of the bending, i.e., the deflection is approximated by the following equation:

$$\text{Deflection} = (FL^3)/(3EI)$$

Specifically, the deflection depends upon the force applied, F, the length L, of arm 1051, the modulus of longitudinal elasticity, E, of arm 1051 and the rectangular moment generated by force F.

During the beginning stages of this insertion, arms 1051 actually provide a resistance force pushing the driver out. Nevertheless, as the driver continues to be pushed in, arms 1051 are bent past a fulcrum point and provide a force pulling the driver and thereby providing the locking force. This is advantageous because the locking force established through self-retaining component 105 is a controlled force in contrast to the friction fit established when using the modified conventional driver with the tapered blade. That is, in contrast to the use of a tapered blade which yields a friction holding force proportional to the force used to establish the friction fit, no matter what force is used to establish the locking force from self-retaining component 105, the locking force is always the same.

The dimension L effects the behavior of arms 1051 as indicated by the equation listed above. The locking force applied by spring arms 1051 also depends upon controlling the dimension T and cross slot width W. If T is too large, then spring arms 1051 will be too rigid and will not be able to bend inwardly to establish the locking force. If T is too small, then spring arms 1051 will not be rigid enough and any locking force established will be insufficient to hold screw 100 to the blade of a driver. Similarly, if W is too large, any locking force established will be insufficient to hold screw 100. In a preferred embodiment, screw 100 is a 1.5 mm titanium screw and the dimension T is controlled to be within 0.008+/−0.0005 inches. These dimensions are based on the material properties, anchor size, and degree of self-retaining strength required.

The dimension D shown in FIG. 10 is also adjustable. More specifically, the dimension D can be reduced to an almost negligible distance without adversely affecting the function of the self-retaining component. That is, spring arms 1051 can extend to the bottom surface 153 as long as the dimensions T and W are controlled as explained above.

Moreover, self-retaining component 105 provides an audible click accompanied by a tactile feedback when the locking force is established. That is, the process of bending spring cantilever arms 1051 past their fulcrum point produces an audible click. Further, the process also can be felt through the handle of the driver so that one can be certain that the locking force has been established.

Figure 11A:
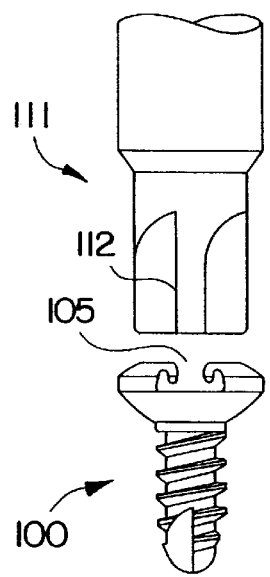
FIGS. 11a and 11b depict an engagement sequence between a conventional driver and a self-retaining screw according to one embodiment of the present invention.
Figure 11B:
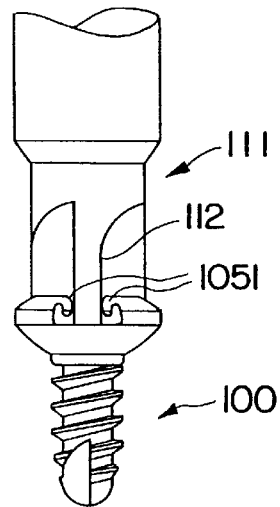
Figure 12A:
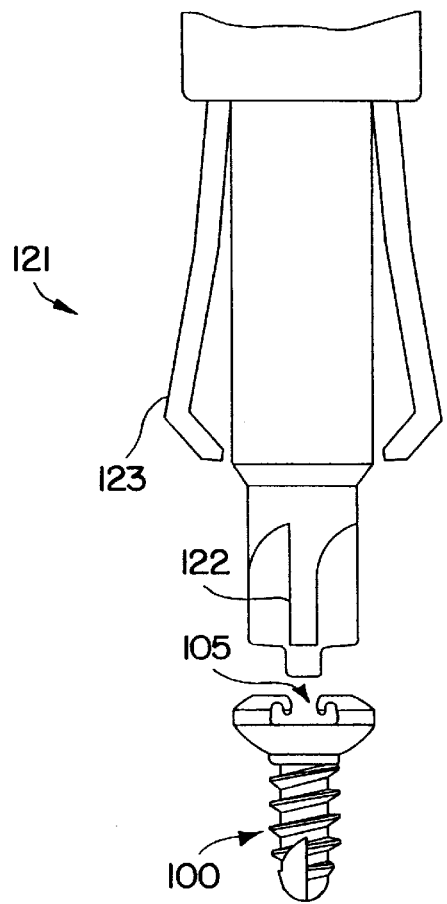
FIGS. 12a and 12b depict an engagement sequence between a conventional driver with a capture device and a self-retaining screw according to one embodiment of the present invention.
Figure 12B:
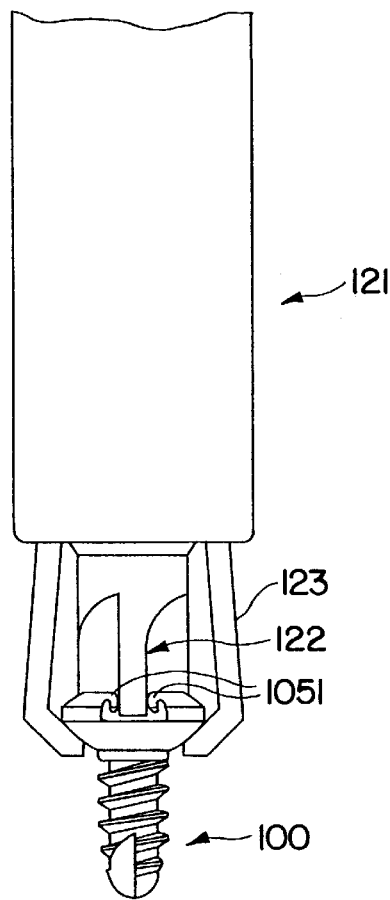
Figure 13A:
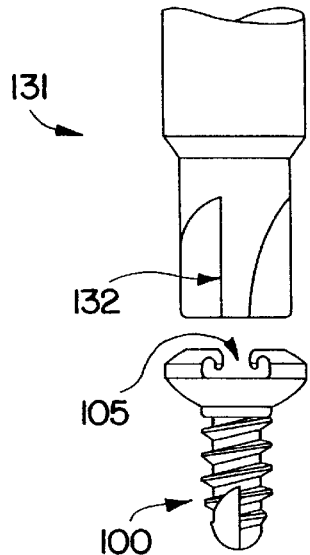
FIGS. 13a and 13b depict an engagement sequence between a conventional flared blade driver and a self-retaining screw according to one embodiment of the present invention.
Figure 13B:
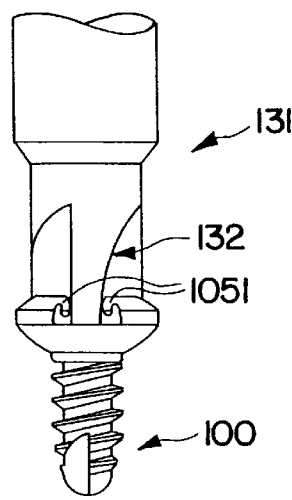

Self-retaining screw 100 is capable of being used with most available drivers. As shown in figures 11, 12 and 13, screw 100 having self-retaining component 105 may be inserted using either of the above described drivers. FIG. 11a–b show use of a conventional driver 111 without clasp mechanism with screw 100 according to the present invention. In FIG. 11b, a controlled friction fit is formed at the interface of driver 111 and spring arms 1051. Note that spring arms 1051 are bent slightly inward providing a slight pulling force on blades 112 of driver 111. FIG. 12a–b show use of a conventional driver 121 with external clamping mechanism 123 with self-retaining screw 100 according to the present invention. In FIG. 12b, a controlled friction fit is formed at the interface of driver 121 and spring arms 1051. Note that spring arms 1051 are bent slightly inward providing a slight pulling force on blades 122 of driver 121. FIG. 13a–b show use of a modified conventional driver 131 with screw 100 according to the present invention. In FIG. 13b, a controlled friction fit is formed at the interface of driver 131 and spring arms 1051. Note that spring arms 1051 are bent slightly inward providing a slight pulling force on tapered blades 132 of driver 131.

Although, self-retaining screw 100 has been introduced in the context of a bone screw, it is not so limited. As is apparent to one of ordinary skill in the art of fasteners from the above explanation, self-retaining component 105 has application in a number of areas. For example, self-retaining component 105 can advantageously be incorporated in fasteners in a general hardware environment such as in conventional metal and wood screws. Moreover, self-retaining component 105 is particularly advantageous in a number of other specialized environments such as in conjunction with the assembly of electronics components, eyeglass screws, and watches. In particular, self-retaining component 105 is advantageously used in conjunction with mass production processes involving robotic insertion of a large number of screws. Incorporation of self-retaining component 105 greatly facilitates such a process by, for example, making it easy for a robotically controlled screw driver to pick up and insert a screw with a minimal chance of process failing. The self-retaining feature is particularly useful in applications where magnetic hold or split grip screwdrivers are impractical such as with non-ferrous materials such as aluminum, plastics, brass, titanium, and stainless steel.

Figure 10C:
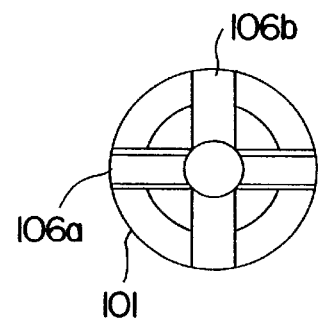

In another embodiment, a combination self-retaining bone screw and suture anchor are provided. Referring again to FIGS. 10a–c, self-retaining screw 100 may also include one or more suture anchor track 15. As described in conjunction with FIG. 1, suture anchor tracks 15 comprise a cavity 151 beneath the top surface 111 of head portion 101 of bone screw 100. Suture anchor tracks 15 include arms 1051 that demarcate cavity 151 and the opening to cavity 151. As previously explained in conjunction with FIG. 1, to anchor a suture, the suture is slipped into slot 16 and through the opening between the tip of arm 1051 and the lower most surface 153 of cavity 151. The width D of the opening between the tip of arm 1051 and the lower most surface 153 of cavity 151 is carefully toleranced to be slightly smaller than the diameter of the suture to be used. Thus, once the suture passes under the tip of arm 1051 it will not easily pass out of cavity 151. Thus, a combination self-retaining bone screw and suture anchor has a structure as shown in FIGS. 1 and 10 with controlled tolerancing of the dimension D (the space between surface 153 and the tip of arm 1051) and the dimension T (the thickness of arm 1051).

Figure 35:
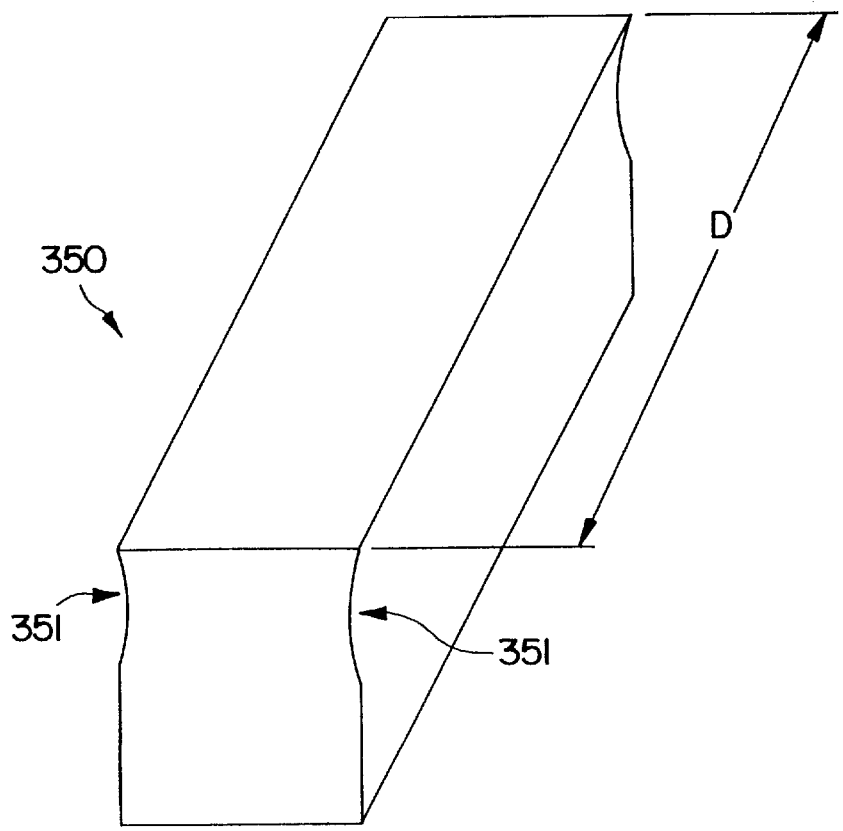
FIG. 35 depicts an apparatus for preventing suture release according to another embodiment of the present invention.

According to another embodiment of the present invention, an apparatus for preventing release of suture from a suture anchor according to the embodiments of the present invention is disclosed. In conjunction with the suture anchors disclosed in the present application it may be desirable to have a fail safe to help ensure that suture does not release from the anchor. FIG. 35 depicts a suture plug 350 for use with a suture anchor according to the embodiments of the present invention. Suture plug 350 is sized for insertion into a slot shaped means for engaging of a suture anchor according to the embodiments of the present invention after suture is anchored within an internal track. Suture plug 350 helps prevent release of suture that is anchored. In the embodiment shown in FIG. 10, suture plug 350 is held in place by the locking force provided by the spring arms of the self-retaining suture anchors disclosed in, for example, the embodiment of FIGS. 10. Accordingly, suture plug 350 includes recessed areas 351 on either side of suture plug 350. Recessed areas 351 engage with the spring arms on the suture anchor. In another embodiment, suture plug 350 is held in place with a mechanical bonding agent such as glue or epoxy. Suture plug 350 typically has a length, L, that is approximately equal to the diameter of the head portion of the suture anchor for which it is being used.

Figure 32:
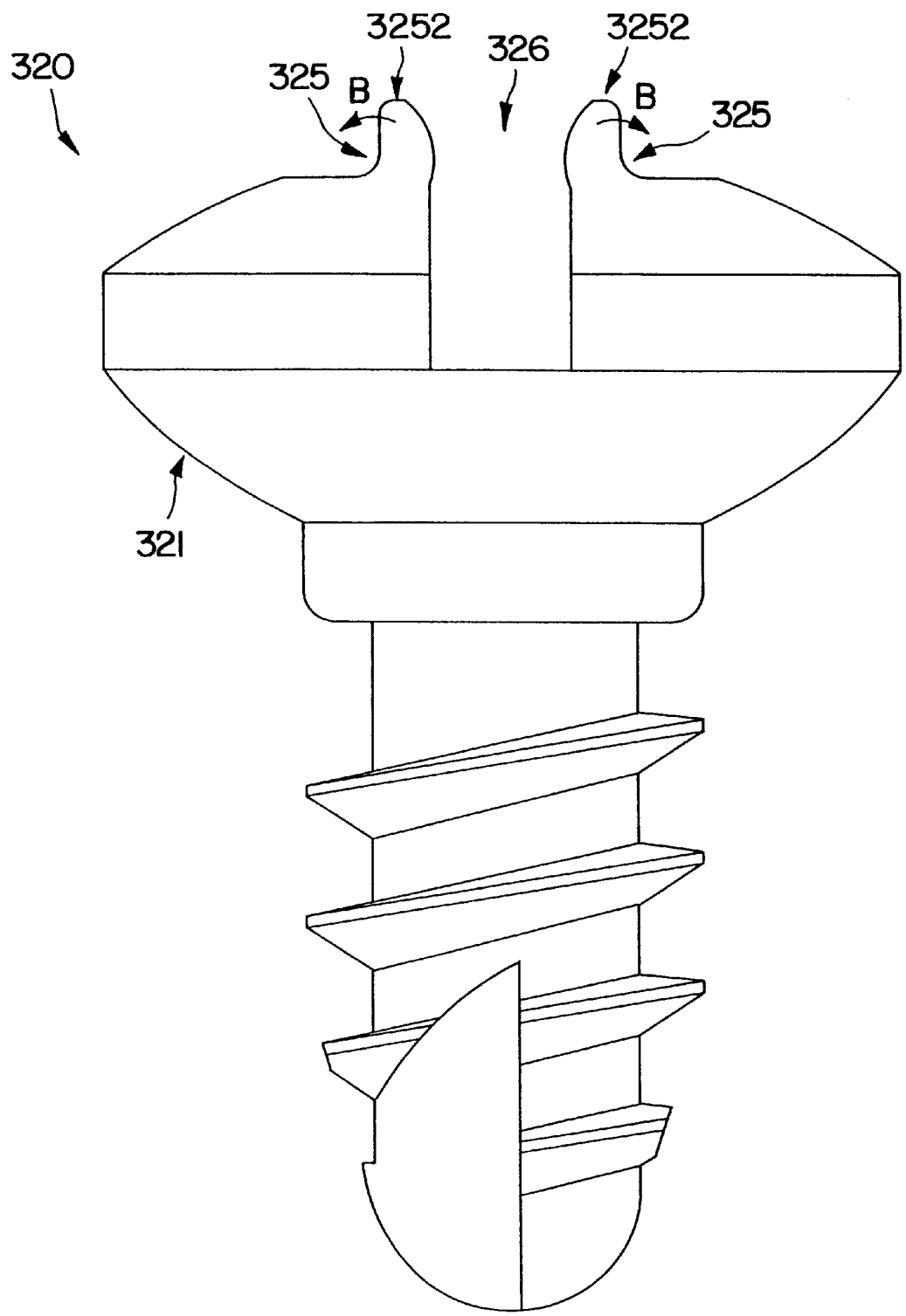
FIG. 32 is a side view of a suture anchor having a male track configuration according to another embodiment of the present invention.

FIG. 32 depicts another embodiment of a combination of self-retaining bone screw and suture anchor. Self-retaining anchor 320 includes a suture anchor having a modified male suture track 325. Suture track 325 is formed by spring arms 3252. Specifically, spring arms 3252 are formed on opposing sides of slot 326 so that, in combination, they form a suture track having a loop configuration surrounding slot 326. Spring arms 3252 thus act as anchoring rails for suture. Moreover, in operation, track 325 is functionally similar to the suture track described above because after engagement with a driver, spring arms 3252 permanently deform in the direction of arrow B to form a defined track 325. Spring arms 3252 also provide self-retaining anchor 320 with its self-retaining characteristic. That is, spring arms 3252 provide a locking force between head portion 321 and a driver inserted into slot 326 of head portion 321. The male track configuration is desirable for manufacturing purposes in that they are made on high-speed heading machines.

Figure 33:
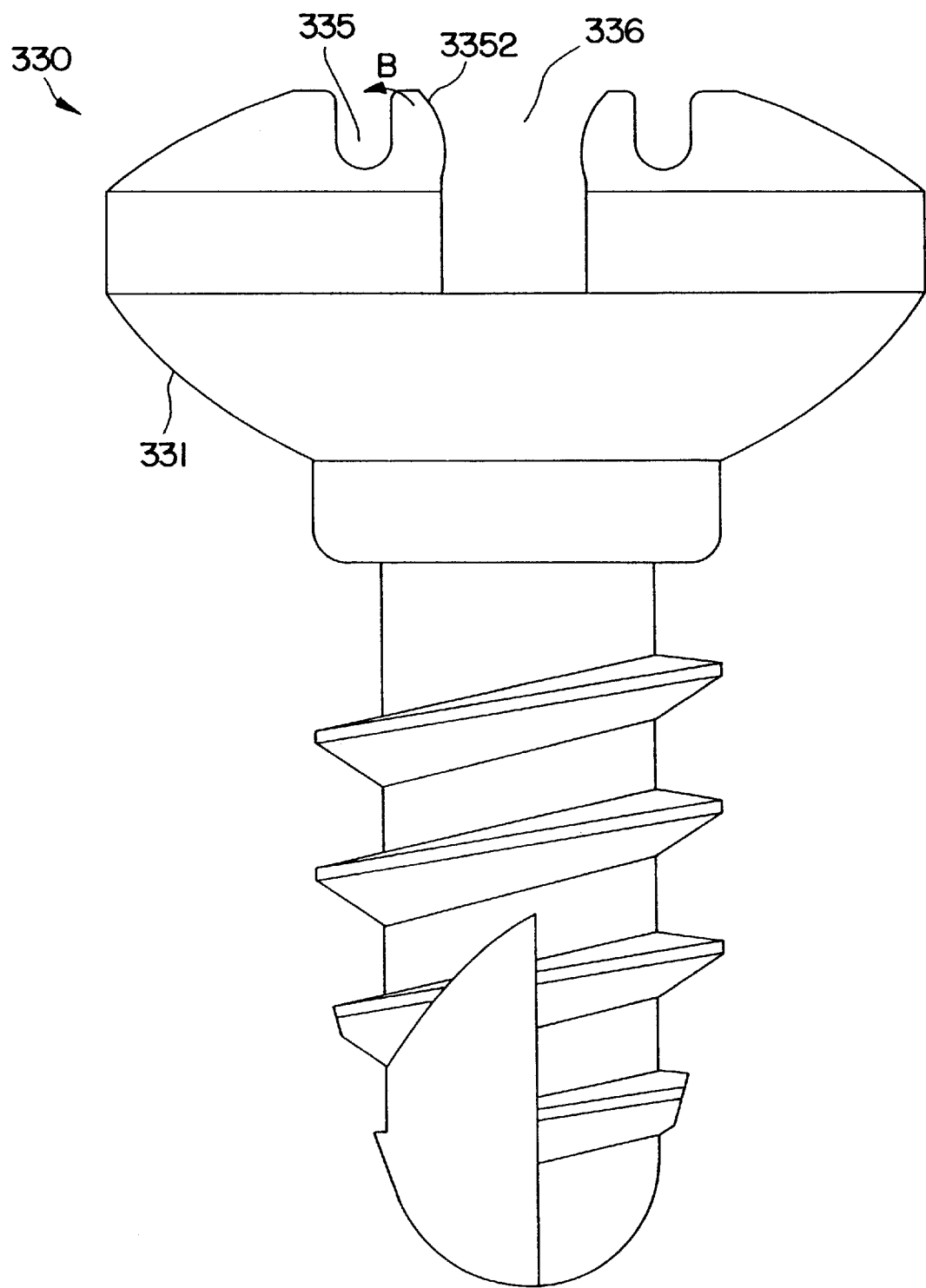
FIG. 33 is a side view of a suture anchor having a male track configuration and a recessed track according to another embodiment of the present invention.

FIG. 33 depicts another embodiment of a combination of self-retaining bone screw and suture anchor. Self-retaining anchor 330 includes a suture anchor having a modified male suture track 335. Suture track 335 is formed by spring arms 3352. Specifically, spring arms 3352 are formed on opposing sides of slot 336 in a recessed area so that, in combination, the recessed areas and spring arms 3352 form a suture track having a loop configuration surrounding slot 336. Similar to the configuration of FIG. 32, spring arms 3352 thus act as anchoring rails for suture. Moreover, in operation, track 355 is functionally similar to the suture track described above because after engagement with a driver, spring arms 3352 permanently deform in the direction of arrow B to form a defined track 335. Spring arms 3352 also provide self-retaining anchor 330 with its self-retaining characteristic. That is, spring arms 3352 provide a locking force between head portion 331 and a driver inserted into slot 336 of head portion 331.

Figure 34:
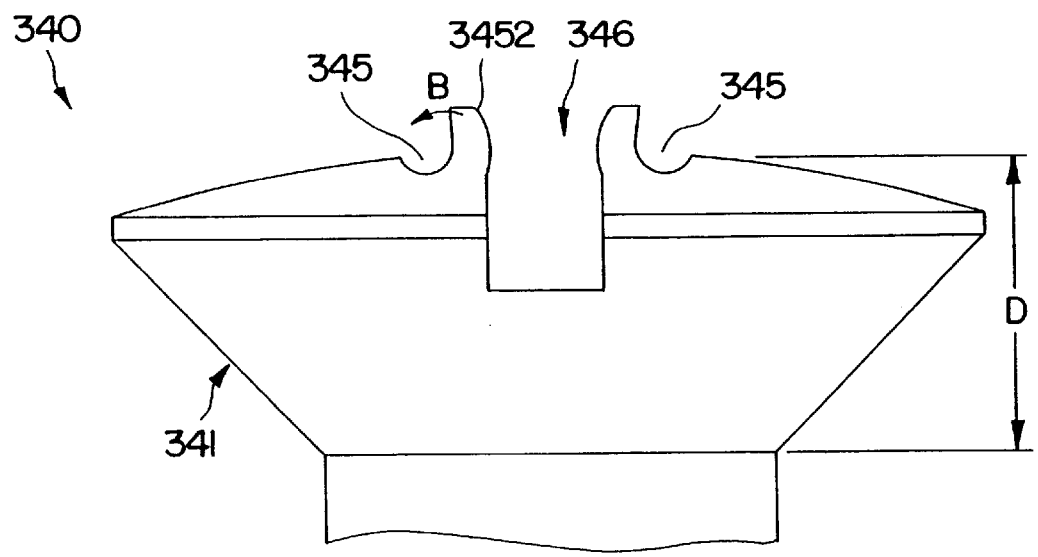
FIG. 34 is a side view of a suture anchor having a male track configuration in a low profile head according to another embodiment of the present invention.

FIG. 34 depicts another embodiment of combined suture anchor and self-retaining bone screw according to another embodiment of the present invention. Self-retaining suture anchor 340 has a reduced head profile D and is thus advantageous for certain environments as explained above. Otherwise, self-retaining suture anchor 340 is structurally and functionally similar to suture anchors 320 and 330 explained in conjunction with FIGS. 32 and 33.

In another embodiment, the present invention relates to a method for using a suture anchor such as the suture anchor described above. Suture anchors can be difficult to use if the suture is permanently attached to the anchor because the suture may be cumbersome when the anchor is being secured into a substrate and the suture may also become tangled during use. A preferred method for using the present invention alleviates both of these problems and is explained in conjunction with FIGS. 36 to 41.

Figure 36:
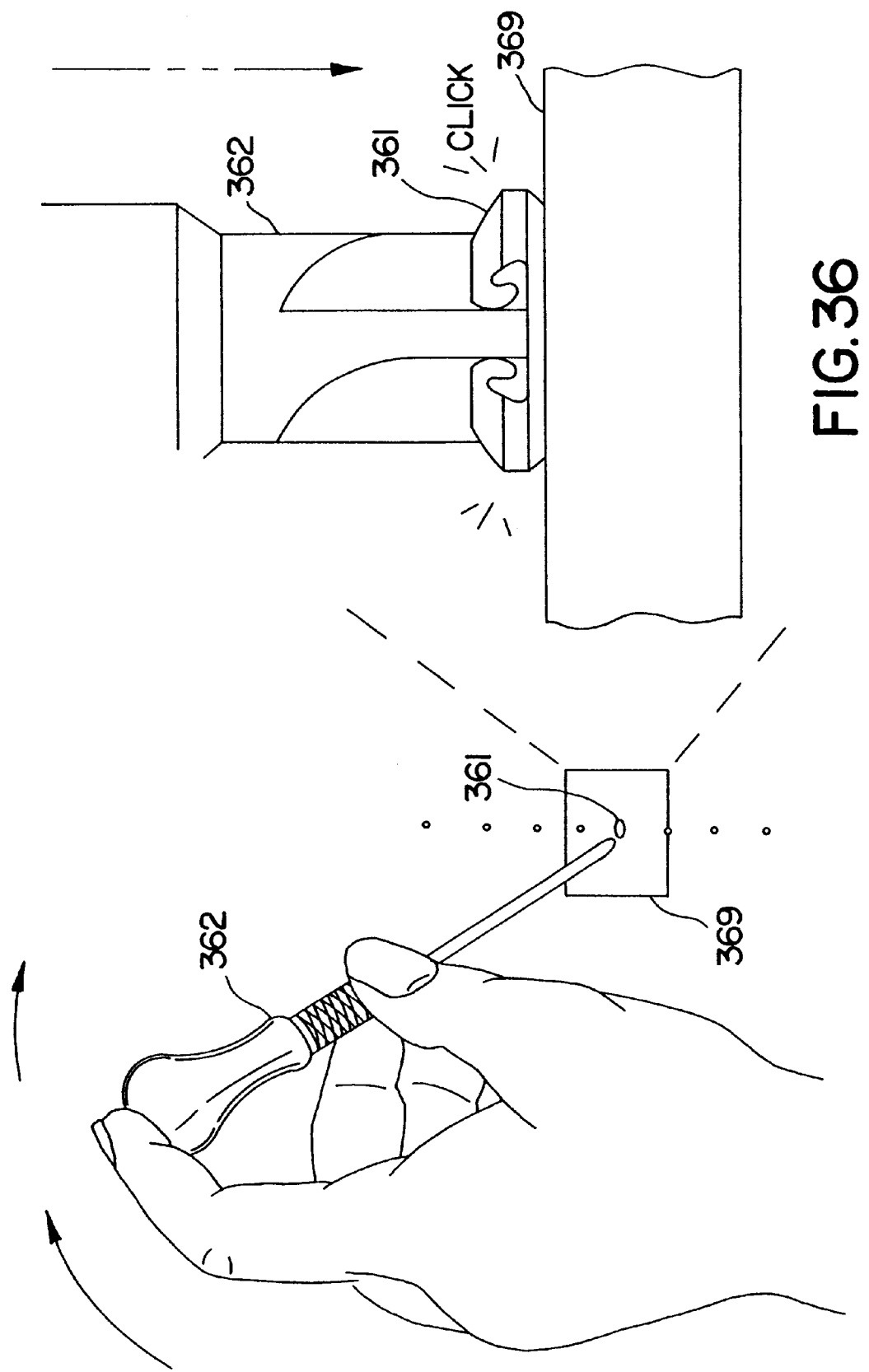
FIG. 36 depicts a step of engaging a driver with a self-retaining suture anchor according to a method of using a suture anchor of the present invention.
Figure 39:
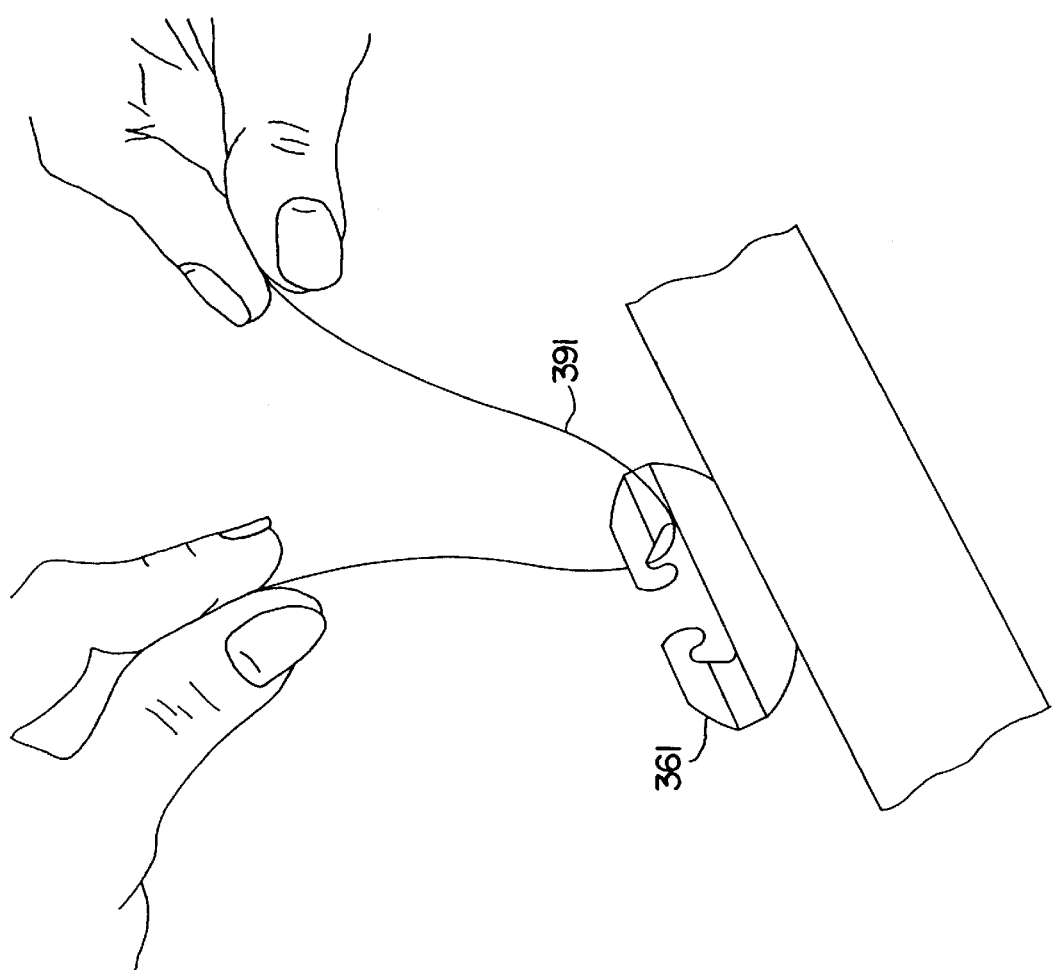
FIG. 39 depicts a step of attaching suture to a self-retaining suture anchor according to a method of using a suture anchor of the present invention.

In an initial step, a driver is engaged with a suture anchor to be inserted into a patient. Typically, suture anchors, such as those described above, are of a very small scale and are thus sterilized and transported within a module. Thus, before being used, the anchor is removed from the module. This step is illustrated in FIGS. 36 and 37 in conjunction with a self-retaining suture anchor as described above. In FIG. 36, a self-retaining suture anchor 361 is engaged with a screwdriver 362 via the self-retaining feature of suture anchor 361. As is indicated in FIG. 36 this is accomplished by rocking the driver into the self-retaining component of suture anchor 361.

According to the method for using a suture anchor of the present invention, suture anchor 361 is then removed from module 369 and screwed into a base material 374 as shown in FIG. 37. As will become apparent, providing base material 374 helps enable some advantageous aspects of the present method to be achieved.

Figure 38:
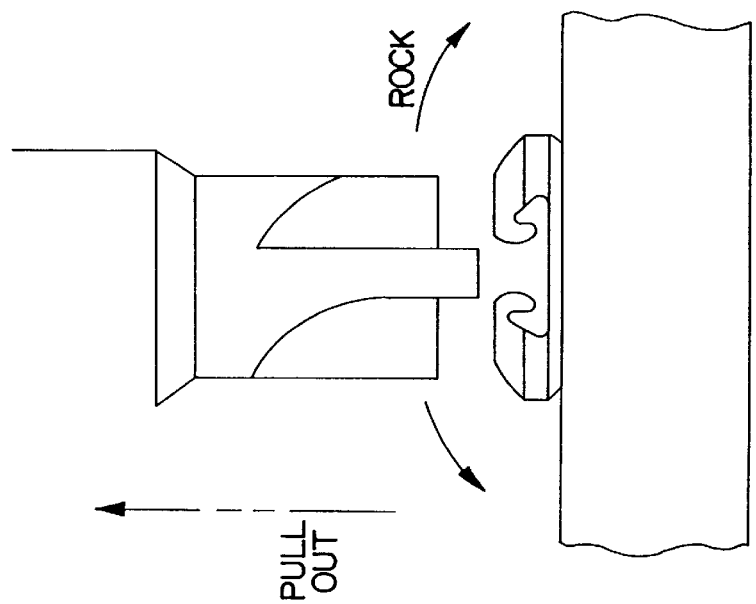
FIG. 38 depicts a step of disengaging a driver from a self-retaining suture anchor according to a method of using a suture anchor of the present invention.

Once suture anchor 361 is screwed into base material 374, screwdriver 362 is disengaged. As shown in FIG. 38, screwdriver 362 is disengaged from base material 374 by a slight bi-directional rock. rocking screwdriver 362. In the embodiment illustrated in FIG. 38, the rocking action loosens the locking force applied to screwdriver 362 by suture anchor 361 thus enabling the disengagement.

Once the suture anchor is positioned within the base material, suture is attached to suture anchor in preparation for insertion into a patient. In one embodiment, shown in FIG. 39, suture material 391 is fitted into the hidden protective track of self-retaining suture anchor 361.

Figure 40:
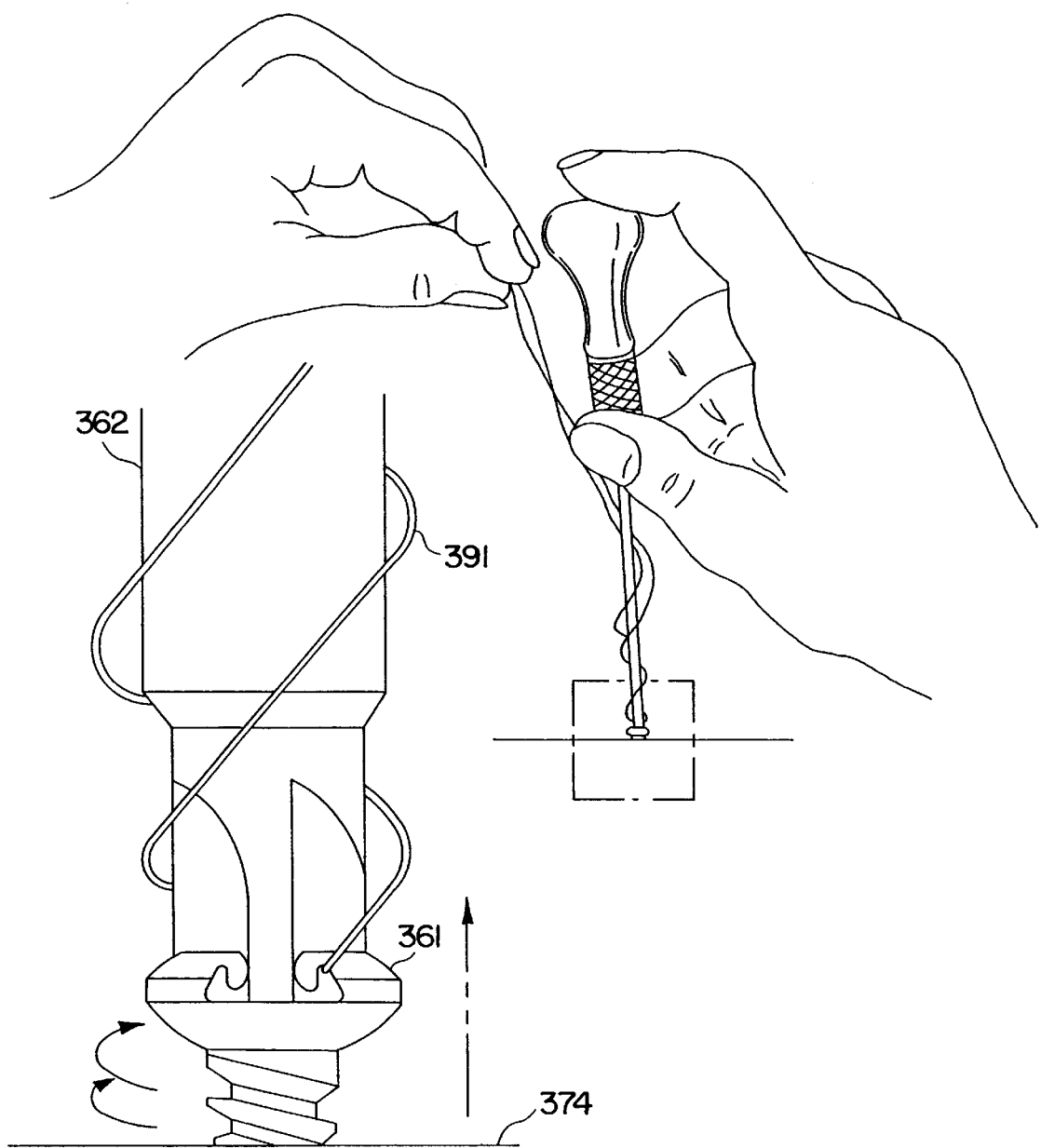
FIG. 40 depicts a step of removing a suture anchor from a base material according to a method of using a suture anchor of the present invention.

In the next step, the screwdriver is re-engaged with the suture anchor and suture material. Once engaged, the suture material is held with the opposing hand and the screw is turned counterclockwise to remove from the base material. As such, the suture material wraps around the driver blade. This step is shown in FIG. 40. As can be seen in FIG. 40, as suture anchor 361 is unscrewed from base material 374, suture material 391 wraps around the blade of driver 362 and is thus positioned so that it will not be in the way when suture anchor 361 is inserted into a patient.

Figure 41:
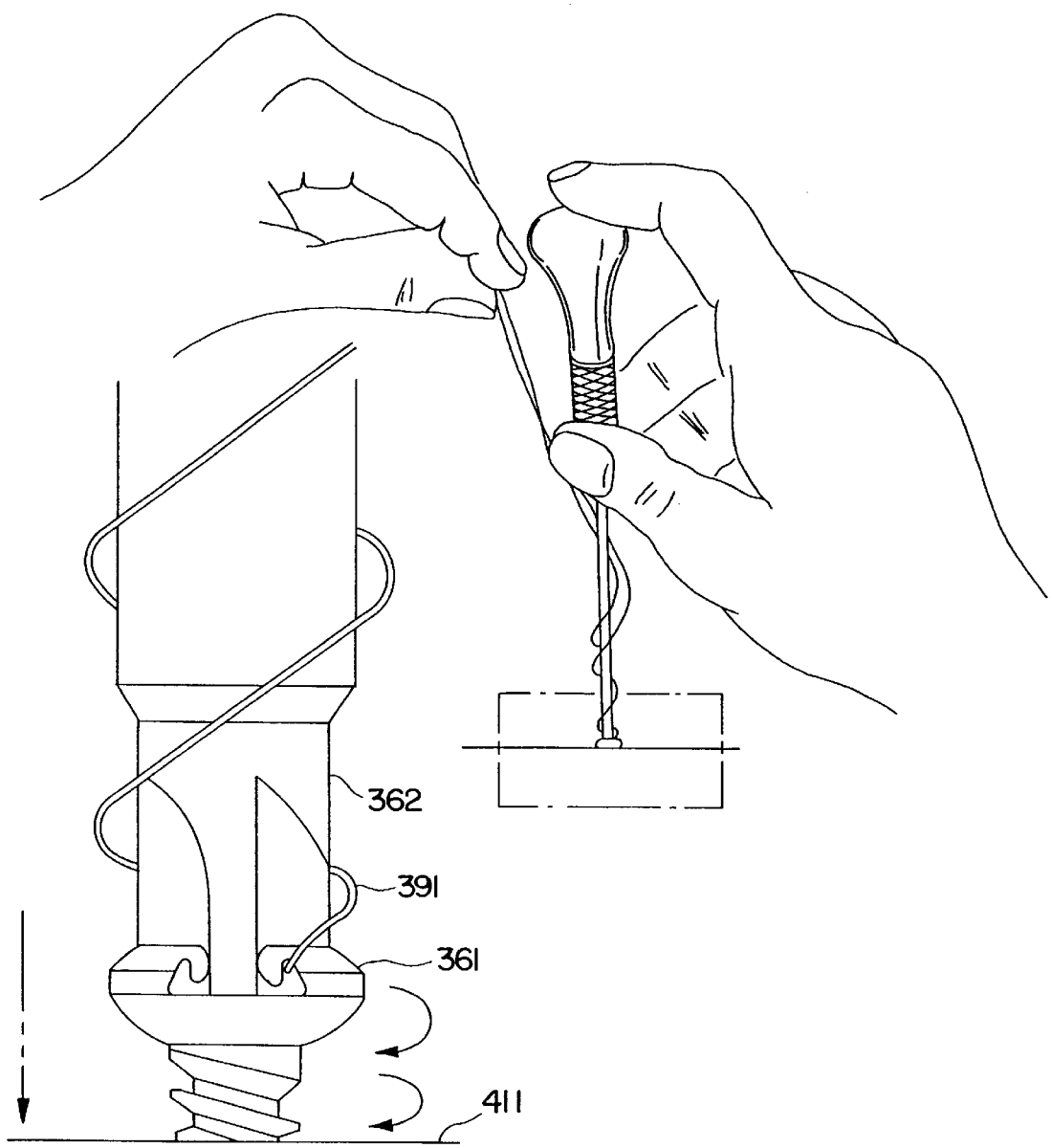
FIG. 41 depicts a step of inserting a suture anchor into a patient according to a method of using a suture anchor of the present invention.

The entire component, including suture anchor, suture, and screwdriver plus blade are then brought to the patient. The suture anchor is inserted into a hole via a clockwise rotational direction. This clockwise rotational direction causes the suture material to unwind from the driver blade. This unwinding mechanism allows a surgeon to know the depth of anchor attachment and provide for a clean release without entangling the suture. This step is shown in FIG. 41. As can be seen in FIG. 41, suture anchor 361 is inserted into bone 411 using a clockwise rotation and thus suture material 391 wound around the blade of driver 362 is unwound and becomes free to use. When suture anchor 361 has been inserted to its desired depth, driver 362 is removed from the head with a bi-directional rock. Suture material 391 is then used to fix soft tissue such as skin, tendon, ligament, and muscle.

According to another embodiment, the present invention provides a process for fabricating general mechanical fastener, such as a suture anchor or self-retaining bone screw as described above. The general steps of this process are depicted in the flow chart of FIG. 14. In an initial step 1410, the structure within which the track is to be fabricated is positioned for fabrication. That is, the structure is positioned to help ensure that the track is fabricated at the proper location within the existing structure. After the structure is positioned, in step 1420a surface of the structure beneath which the track is to be fabricated is prepared. Preparing the surface includes for example leveling the surface beneath which the track is to be incorporated to account for non-uniformities in the surfaces. In step 1430, the track is fabricated beneath the prepared surface. And, in step 1440 (optional) a precision, self-drilling tip is fabricated on the structure.

The preparation and fabrication steps may be accomplished using a number of different fabrication techniques such as, mechanical deformation techniques, powder metal techniques, water jet, photo etching, laser, broaching, sawing, molding, conventional or wire electrical discharge machining (EDM) process. EDM is a will known process in which an electrical discharge is used to essentially burn away unwanted material. One particular mechanical deformation technique that could be used is cold-heading. Cold-heading is a stamping process that could be used to mass produce screws for industrial applications.

In a preferred embodiment, a wire EDM process is used to prepare the surface and fabricate the track and tip by using a wire burn. The wire EDM process is especially important when applied to materials that have mechanical properties that limit their machinability such as bioabsorbable and biodegradable materials. The wire EDM process is equally important when applied to materials which are extremely hard and durable such as titanium, cobalt chromium and diamond. Each of the steps of FIG. 14 will now be explained in more detail in conjunction with a preferred embodiment of fabricating an internal track and precision tip on a screw to be used, for example, as a self-drilling suture anchor track or self-retaining bone screw as explained above.

In step 1410, a blank or screw blank is positioned for fabrication of track and tip. A screw blank is a screw that does not yet have a completed means for engaging with a screw driver. A blank is a screw that has neither a means for engaging a driver or any threaded portion. Unless specifically excepted, the term screw as used hereinafter is meant to refer to both screws and screw blanks. In a preferred embodiment, this process for fabricating a track within an existing structure is a mass production process. That is, the process is performed on a number of screws simultaneously. Therefore, step 1410 is actually performed on a number of screws simultaneously.

Figure 15:
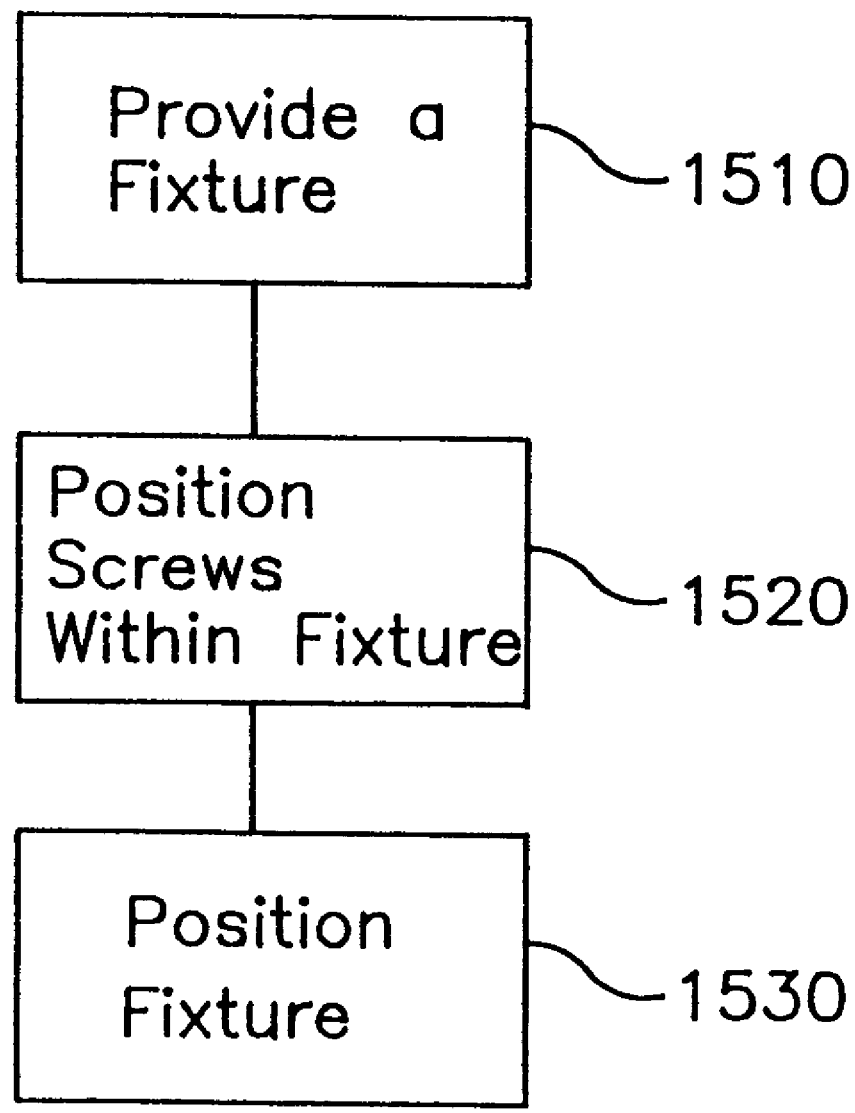
FIG. 15 depicts a flow chart for the step of positioning a structure shown in FIG. 14.

In a preferred embodiment, step 1410 involves a number of sub-steps and will be explained in conjunction with FIGS. 15 and 16. Referring to FIGS. 16a–d, according to a preferred embodiment, in step 1510, a fixture 1610 is provided to position a plurality of screws for surface preparation (step 1420), track fabrication (1430) and tip fabrication (1440). Fixture 1610 comprises a matrix of holes 1611 used to position screws for fabrication. In the embodiment shown in FIGS. 16, the matrix of holes 1611 comprises twenty rows and twenty columns within which screws can be positioned for surface preparation and track and tip fabrication. Nevertheless, fixture 1610 may have any number of holes 1611 or tracks (within which a number of screw blanks are positioned). Fixture 1610 is configured for fabricating a track and/or a tip on a screw. Nevertheless, fixture 1610 can be modified to accommodate structures such as plates, washers, general surgical implants, fasteners, etc. Fixture 1610 is preferably fabricated of a conductive material, i.e. a conductive polymer or metal. As one of ordinary skill in the art will recognize, electrical conductivity is important for the wire EDM process because the process relies on the passage of electrical current to create a plasma field around the wire which burns the surrounding material.

Moreover, fixture 1610 is constructed such that height, flatness, squareness, concentricity, surface finish and position are precisely controlled and modifiable. In one embodiment, each hole 1611 within fixture 1610 may be counter sunk to a uniform depth so that the screws 1613 are positioned within holes 1611 (explained below) they protrude above the surface of fixture 1611 a controlled distance.

In step 1520, screws 1613 within which a track and tip are to be fabricated, are positioned within holes 1611 of fixture 1610. More specifically, screws 1613 are aligned and secured within holes 1611. In one embodiment, screws 1613 are slot-head screws and therefore, screws 1613 are advantageously positioned so that the slots in their heads are aligned for the step of track fabrication. That is, because the track is generally fabricated in general alignment with the slot of a slot head screw as explained in conjunction with FIG. 1, the heads of screws 1613 should be positioned so that their slots have a known alignment. Alignment of screws is not as important if screw blanks are used.

Once screws 1613 are positioned in fixture 1610, screws 1613 are secured within fixture 1610. Securing the screws within fixture 1610 is accomplished by various mechanical or chemical bonding techniques. Direct mechanical attachment is achieved by screwing the screw into fixture 1610 or by a similar clamping/interference mechanism. In one embodiment, a mechanical interface comprising metal fingers is used to secure screws 1613 within fixture 1610. FIG. 17 depicts a portion of fixture 1610 including clamps 1711. Clamps 1711 include a number of fingers 1712 positioned to align with slots of screw 1613 when placed within holes 1611. Clamps 1711 are fastened to fixture 1610, for example by screwing and thus fingers 1712 aligned with slot of screws 1613 secure screws 1613 to fixture 1610.

In another embodiment, screws 1613 are secured to fixture 1610 by chemical/mechanical bonding. Chemical/mechanical bonding is achieved by applying an adhesive or epoxy to fixture 1610 and screws 1613. Such attachment allows for secure positioning of screws 1613 within fixture 1610. Electrical conductivity is achieved by wiring the screws to one another or through a conductive epoxy. Mechanical fixation, for example by screwing or using clamps 1711, provides for direct electrical contact between screws 1613 and fixture 1610.

In another embodiment, sub-fixture attachment is used to secure screws 1613 to fixture 1610. For example, in one embodiment screws 1613 are screwed to an encapsulated dowel 1811 within fixture 1610. FIG. 18 shows a portion of fixture 1610 that has been modified to accept an encapsulated dowel 1811. As can be seen from FIG. 18a, in this embodiment, screws 1611 are secured to fixture 1610 by screwing them into encapsulated dowel 1811. Encapsulated dowel 1811 can be made of, for example, wood or polymer. The dowel cannel can also be backfilled with a locking material such as a conductive epoxy. Large holes are either dowel holes or securing holes. Other ways of securing screws 1613 to fixture 1610 are possible and are considered within the scope of the present invention and include but are not limited to solder, vacuum, spring washers, and magnetic interface.

FIGS. 29 depict an alternative fixture having a collet clamping mechanism that may be used as an alternative to fixture 1610. The first step in the collet fixture process is placement of screw into collet jaw 2911. Screw 1613 is placed into collet jaw 2911 by applying a force F, shown in FIG. 29*c*, to open collet jaw 2911. Once screw blank 1613 is loaded into collet jaw 2911, the force F is removed and collet jaw 2911 retracts into fixture 2911. The clamping mechanism looks very similar to mechanisms used within the standard mechanical pencil to advance and hold the graphite. The opposing force on the collet or locking force is produced by a spring, nut or external pressuring device which pulls the collet back. The back pressure results in a secure clamp to the screw blank.

As mentioned above, maintaining electrical contact is important for the wire EDM process because the process relies on the passage of electrical current to create a plasma field around the wire which burns the surrounding material. Electrical contact via the chemical holding process is achieved by using a conductive tape, adhesive, gel, epoxy, conductive wire (that is, wiring each screw blank to the fixture), conductive ink, or similar. For example after screws 1613 are place within fixture 1610, a portion of the threaded portion of the screw will protrude through the fixture 1610. In one embodiment, these end portions are secured to fixture 1610 using conductive epoxy. In one embodiment, an acid etch is used before epoxying so that the epoxy sticks to screw blanks 1613. Electrical contact is also achieved by the mechanical interface that results from the chemical bonding.

In step 1530, fixture 1610 is positioned. That is, within the context of a mass production process it is desirable to position fixture 1610 so that a track and tip can be uniformly fabricated on all of screws 1613. To help ensure this uniform fabrication, in step 1530, fixture 1610 is positioned so that the cutting element used in the preferred wire EDM process is parallel with the rows of screws 1613 within the matrix of holes within fixture 1610. Fixture 1610 is positioned and held using positioning and holding holes 1612 arranged around the outside and in the center of fixture 1610. More specifically, positioning holes 1612 enable rotation of fixture 1610 via dowel pins, while maintaining the established positioning of screws 1613 within fixture 1610. This rotation component provides for accurate positioning of fixture 1610 on two axis such that different geometric configurations can be fabricated within screws 1613. The rotation also allows for fabrication of internal and external geometric configurations within the heads and on the tips of screws 1613 such as are shown in the figures described above.

Figure 19:
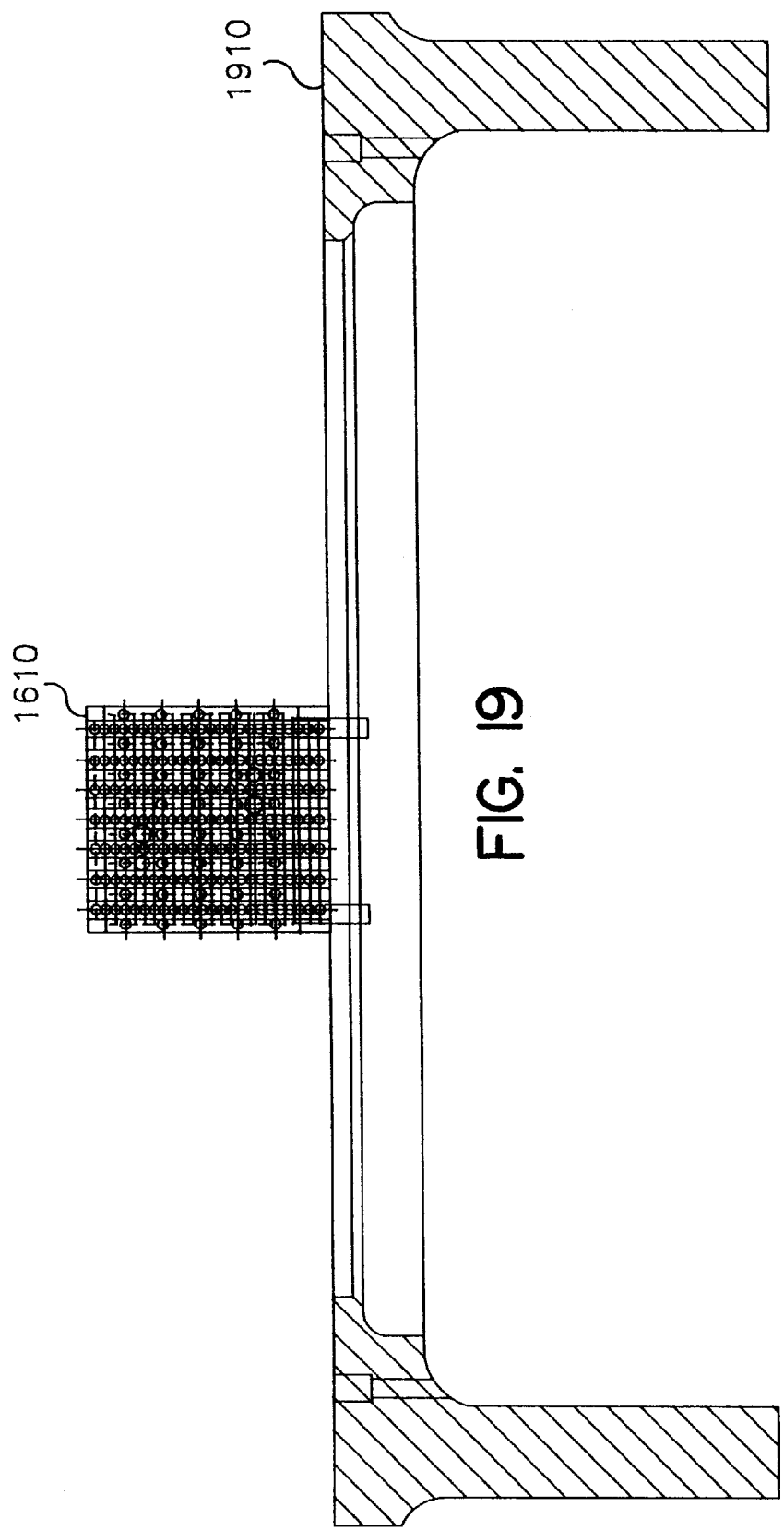
FIG. 19 depicts a fixture positioned on a wire EDM table.

Typically fixtures 1610 are stacked around the table of a wire EDM machine to facilitate unattended or semi automated manufacturing. For example, FIG. 19 shows a fixture 1610 positioned on a wire EDM table 1910. Fixture 1610 is made such that it interfaces with an angle bracket allowing rapid change over. Fixture 1610 is made such that it may be used in some other mass production machine. That is, fixture 1610 is a general fixture that may be used to process a number of blanks through other mass production steps such as, deburring.

Returning to FIG. 14, in step 1420 a surface of screws 1613 is prepared for track fabrication. Surface preparation is necessary to account for non-uniformities in the configuration of the heads of screws 1613. As is known to one of ordinary skill in the art, wire EDM fabrication involves moving a wire along a predetermined path to fabricate the desired configuration. In the preferred embodiment of the present invention wire EDM is used to simultaneously fabricate a track and tip in a plurality of screws aligned in a row. If the screws aligned in a row have non-uniformities in, for example, the thickness of their head portions, the wire EDM process will not as accurately fabricate a track or tip in each of the screw heads within the row. That is, the track will be deeper in some screw heads and shallower in others. To account for these non-uniformities, in step 1420 the screw head surfaces are prepared by making a skim cut across the surface of all the screw heads in a row.

Figure 20A:
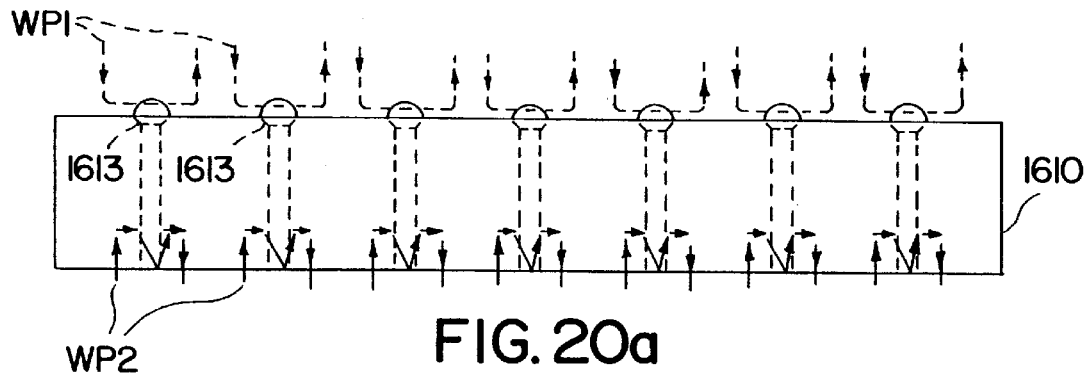
FIGS. 20a and 20b depicts a step of preparing a surface for fabricating a track within an existing structure and a step of fabricating an end portion on a threaded portion of a mechanical fastener according to one embodiment of the present invention.
Figure 20B:
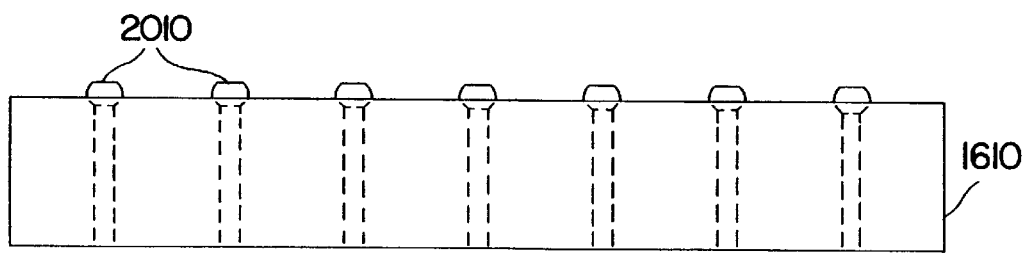

FIGS. 20 show side views of fixture 1610 before (FIG. 20*a*) and after (FIG. 20*b*) the surfaces of the screw heads have been prepared. In FIG. 20*a*, the wire path, WP, for performing a skim cut using the wire EDM process is shown. As can be seen from FIG. 20*a*, wire path WP simultaneously cuts across the surface of each screw head within a row of the matrix. FIG. 20*b* shows screws 2010 having a prepared head. As can be seen from FIG. 20*b*, the heads of screws 2010 have a uniform thickness thus enabling tracks to be fabricated within each screw head in a row in a uniform manner. In a preferred embodiment, the wire used in the wire EDM process has a length sufficient to extend along an entire row of the matrix of holes 1611 so that the surface of each screw 1613 within a row is prepared simultaneously.

Figure 21:
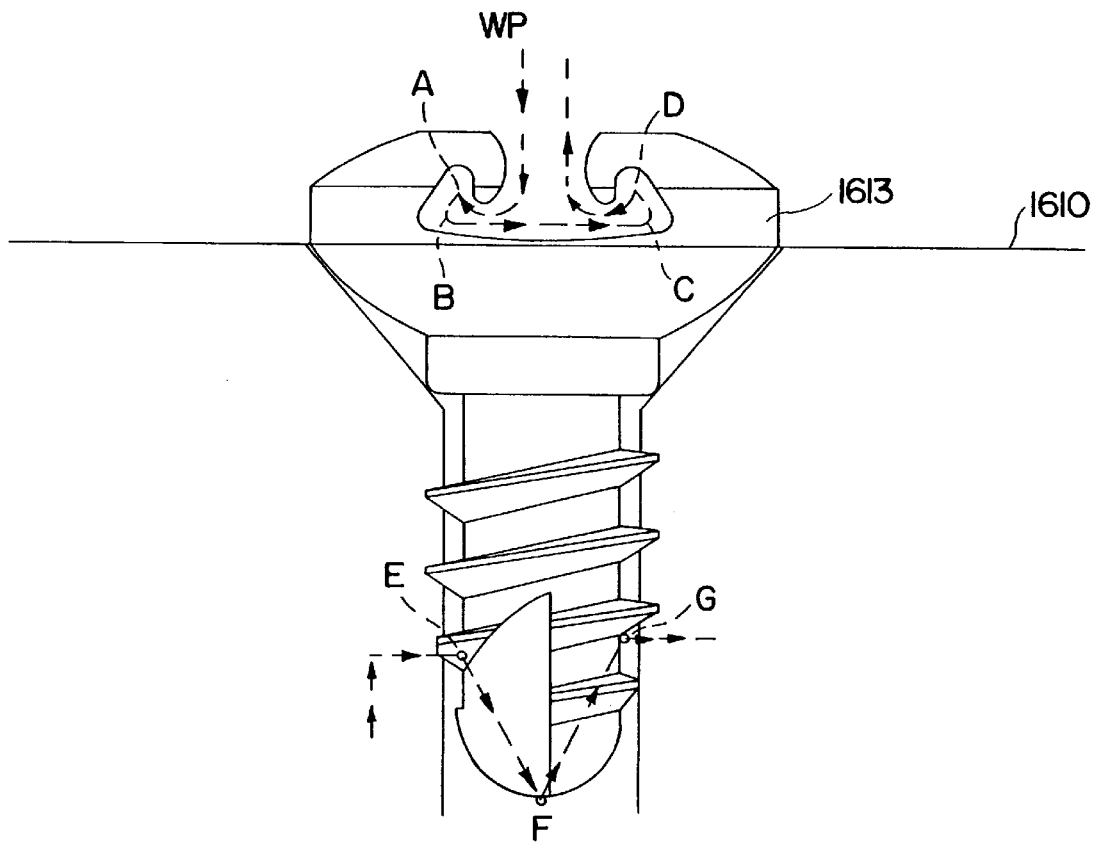
FIG. 21 depicts a step of fabricating a track within an existing structure and/or a step for fabricating an end portion on a threaded portion of a mechanical fastener according to one embodiment of the present invention.

In step 1430, a track is fabricated beneath the surface of the head of each screw within a row. In a preferred embodiment, a track is fabricated using a wire EDM process. The step of fabricating a track is explained in more detail in conjunction with FIG. 21. FIG. 21 is an exploded view of a screw 1613 within fixture 1610 and shows the path, WP1, of the wire of the EDM process. As shown in FIG. 21, in order to fabricate the track according to the present invention within the head of screw 1613 the wire follows a path down into the head of the screw, up and under to a point A, down to the lower surface of the track at a point B, across the bottom surface of the track to a point C, up and under to a point D and then under and out of the head. In a preferred embodiment, the wire used in the wire EDM process has a length sufficient to extend along an entire row of the matrix of holes 1611 so that a track is fabricated within the head of each screw 1613 within a row simultaneously.

Figure 14:
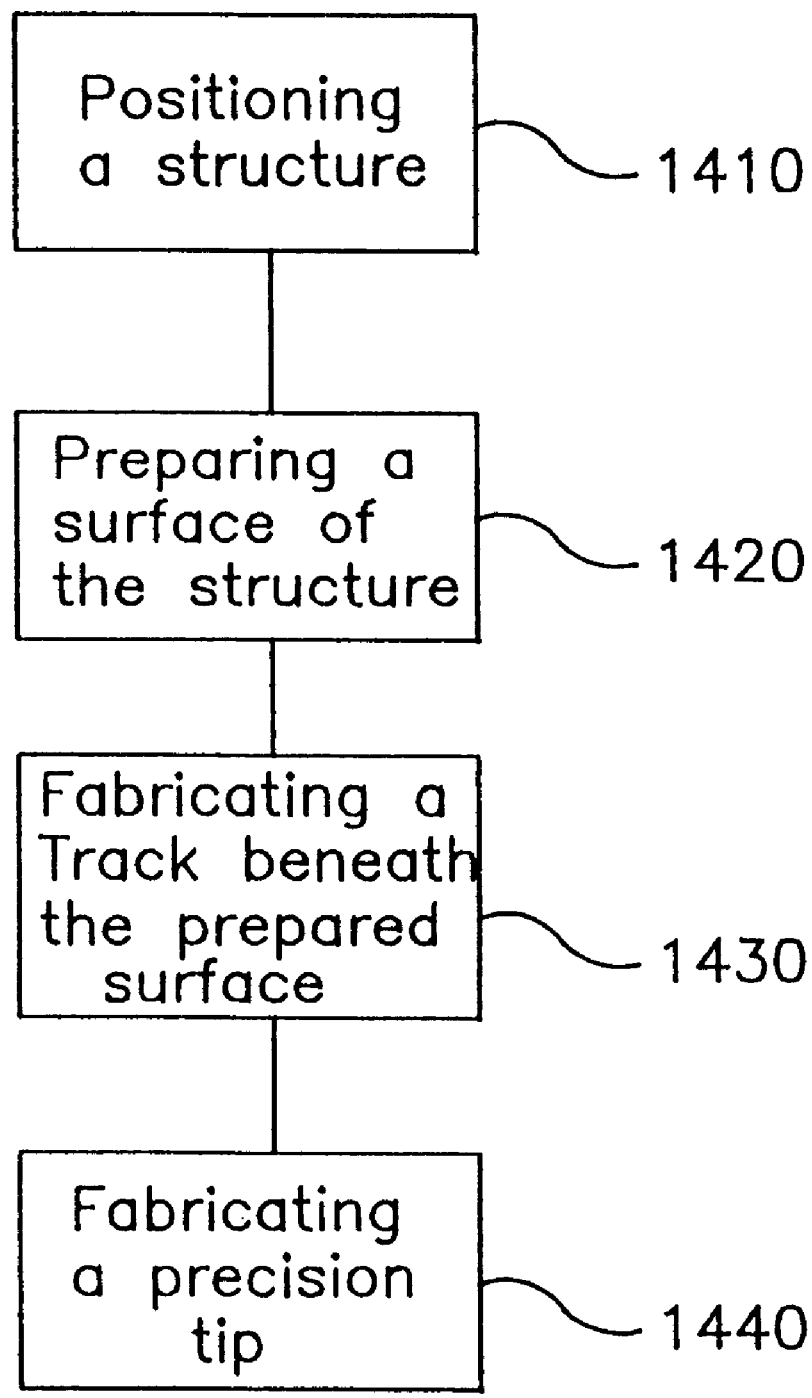
FIG. 14 depicts a flow chart for a process for fabricating a track within an existing structure according to one embodiment of the present invention.

Referring a final time to FIG. 14, a precision tip is then fabricated on the tip of each screw within a row. A self-drilling component, such as component 24 shown in FIG. 2 requires a sharp edge. Often, conventional processes do not produce a sufficiently sharp edge. An edge that is dull or not sufficiently sharp can lead to cracking of the material into which the self-drilling component is being inserted. This is extremely undesirable when the material is a human bone. Therefore, according to another embodiment of the present invention, a wire EDM process is used for fabricating a self-drilling component. Moreover, the use of the EDM process is also beneficial for fabricating a self-drilling component because it minimizes the mechanical stress induced on the tip as compared to conventional fabrication processes such as grinding.

Specifically, in one preferred embodiment, a self-drilling component is fabricated in step 1440. In this embodiment, after the track is fabricated in step 1430 of FIG. 14, a self-drilling component is fabricated at the tip of the screw blank. In a preferred embodiment, the wire used in the EDM process is indexed to the back side of fixture 1610. The wire is then used to cut the self-drilling component in the tip of the screw blank following wire path WP2 shown in FIGS. 20 and 21. As shown in FIG. 21, in order to fabricate the precision tip the wire follows the path up to a point along the body of the screw at E, down across the tip to a point F, back up across the tip to a point G and the out and away from the tip. This is merely one example of a wire path to cut a precision, self-drilling tip. Many other configurations are also possible as are indicated in FIG. 42 and 43. The use of the wire EDM process to cut the self-drilling component provides a precision tip having an edge that is sharper than that obtained by conventional manufacturing processes. Moreover, the use of the wire EDM process is advantageous because it is easily combined with the process for fabricating a track disclosed in conjunction with steps 1410 to 1430 of FIG. 14.

In other embodiments, the wire path is adjusted to fabricate different configurations of tracks and tip or to fabricate only a single track. After, the tracks are fabricated, fixture 1610 may be rotated 90 degrees or any angle in-between using positioning holes 1612 in order to fabricate a transverse slot or track into the head of screw 1613 or to fabricate another side of the tip. For example, the different tip configurations shown in FIG. 43 can be fabricated after rotation. Specifically, the configurations marked "a," "c," "e," and "g" in FIG. 43 can be fabricated initially. These initial configurations can then be combined with any of the configurations marked "b," "d," "f" and "h" after fixture 1610 is rotated 90 degrees. Moreover, when screw blanks are used, the screw blanks are initially slotted by the wire EDM process or other machining process.

Although the present invention has been described in detail, it is understood by those skilled in the art that various changes, substitutions, and alterations can be made without departing from the intended scope as defined by the appended claims.

What is claimed is:

1. A mechanical fastener comprising:
   an elongate member having a first end and a head portion, said first end adapted for insertion into a substrate, said head portion having at least one surface and comprising means to engage with a driver; and,
   at least one arm formed within said head portion, said arm having an outer surface integral with an outer surface of said head portion and an inner surface including a projection at an end of the arm.

2. The mechanical fastener of claim 1 wherein said at least one arm comprises at least one spring arm formed within said head portion adjacent the means to engage with a driver, the at least one spring arm providing a locking force between said head portion and a driver.

3. The mechanical fastener of claim 2 wherein the locking force is generated by a displaced moment arm of the spring arm.

4. The mechanical fastener of claim 2 wherein said means to engage with a driver provides an audible and tactile confirmation that the locking force between said head portion and said driver has been established.

5. The mechanical fastener of claim 2 wherein said means to engage with a driver comprises a slot within said upper surface of said head portion, said at least one spring arm positioned in general alignment with one side of said slot.

6. The mechanical fastener of claim 2 wherein said means to engage with a driver comprises transverse slots within said upper surface of said head portion, said at least one spring arm positioned in general alignment with one side of one of said transverse slots.

7. The mechanical fastener of claim 2 wherein said means to engage with a driver comprises a square shaped cutout within said upper surface of said head portion, said at least one spring arm positioned in general alignment with one side of said square shaped cutout.

8. The mechanical fastener of claim 2 wherein said means to engage with a driver comprises a cutout within said upper surface of said head portion, said at least one spring arm positioned in general alignment with a side of said cutout.

9. The mechanical fastener of claim 2 wherein the at least one spring arm comprises a track formed within said head portion below said outer surface of said head portion, said track operative to anchor at least one suture without through threading.

10. The mechanical fastener of claim 9, wherein said means to engage with a driver comprises a slot within said head portion and said track is incorporated within an internal portion of said head portion to one side of the slot, said slot and said track forming a continuous void within said head portion.

11. The mechanical fastener of claim 9, further comprising a second track formed within said head portion below said outer surface of said head portion.

12. The mechanical fastener of claim 11, wherein said means to engage with a driver comprises a slot within said head portion and said track and said second track are incorporated in said head portion on opposite sides of the slot, said slot, said track and said second track forming a continuous void within said head portion.

13. The mechanical fastener of claim 11, wherein said means to engage with a driver comprises transverse slots within said head portion and said track and said second track are incorporated in said head portion on opposite sides of one of the slots, and said slots, said track and said second track forming a continuous void within said head portion.

14. The mechanical fastener of claim 9, wherein said means to engage with a driver comprises a cutout within said head portion and said track is incorporated in said head portion through said cutout, and said cutout and said track forming a continuous void within said head portion.

15. The mechanical fastener of claim 9, wherein said means to engage with a driver comprises a square shaped cutout within said head portion and said track is incorporated in said head portion through said square shaped cutout, and said square shaped cutout and said track forming a continuous void within said head portion.

16. The mechanical fastener of claim 9, wherein said outer surface of said head portion comprises a peripheral surface of said head portion, and said track is incorporated around said peripheral surface of said head portion.

17. The mechanical fastener of claim 16 further comprising a port intersecting said track and providing an anchor point for a suture on said track.

18. The mechanical fastener of claim 9, wherein said outer surface of said head portion comprises an underside surface of said head portion, and said track is incorporated in said head portion beneath said underside surface.

19. The mechanical fastener of claim 1, wherein said elongate member comprises a low carbon, corrosion-resistant, non-magnetic material.

20. The mechanical fastener of claim 1, wherein said elongate member comprises a reabsorbable implant material.

21. The mechanical fastener of claim 1, wherein said elongate member comprises Titanium.

22. The mechanical fastener of claim 1, wherein said elongate member comprises stainless steel.

23. The mechanical fastener of claim 1, wherein said elongate member comprises cobalt chrome.

24. The mechanical fastener of claim 1, wherein said elongate member comprises a bone screw that can be removed and reinserted without damaging substrate.

25. The mechanical fastener of claim 1, wherein said elongate member comprises a bone screw sized for insertion into a particular anatomical area.

26. The mechanical fastener of claim 1, further comprising a surgical plate, said surgical plate attached to a substrate by said elongate member.

27. The mechanical fastener of claim 1 wherein said first end comprises a tapered self-tapping portion.

28. The mechanical fastener of claim I wherein said first end comprises a self-drilling portion.

29. The mechanical fastener of claim I wherein said elongate member comprises a threaded portion.

30. The mechanical fastener of claim I wherein said elongate member comprises a barbed portion.

31. A self-retaining screw comprising:
an elongate member having a first end and a head portion, said first end adapted for insertion into a substrate, said head portion having an upper surface;
means for engaging said screw with a driver formed within said head portion; and,
at least one spring arm formed within said head portion adjacent the means for engaging, the at least one spring arm providing a locking force between said head portion and said driver.

32. The screw of claim 31 wherein the locking force is generated by a displaced moment arm of the spring arm.

33. The screw of claim 31 wherein said means for engaging provides an audible and tactile confirmation that the locking force between said head portion and said driver has been established.

34. The screw of claim 31 wherein said means for engaging comprises a slot within said upper surface of said head portion, said at least one spring arm positioned in general alignment with one side of said slot.

35. The screw of claim 31 wherein said means for engaging comprises transverse slots within said upper surface of said head portion, said at least one spring arm positioned in general alignment with one side of one of said transverse slots.

36. The screw of claim 31 wherein said means for engaging comprises a square shaped cutout within said upper surface of said head portion, said at least one spring arm positioned in general alignment with one side of said square shaped cutout.

37. The screw of claim 31 wherein said means for engaging comprises a cutout within said upper surface of said head portion, said at least one spring arm positioned in general alignment with a side of said cutout.

38. A self-drilling suture anchor comprising:
an elongate member having a first end and a head portion, said first end adapted for drilling into and securing the elongate member within a substrate, said head portion having at least one surface and comprising means to engage with a driver; and
anchoring means formed within said head portion operative to anchor at least one suture without through threading
wherein said means to engage with a driver comprises a slot within said head portion and said anchoring means is incorporated within an internal portion of said head portion, said slot and said anchoring means forming a continuous void within said head portion.

39. The self-drilling suture anchor of claim 38, wherein said means to engage with a driver comprises transverse slots within said head portion and said anchoring means is incorporated within an internal portion of said head portion, said slots and said anchoring means forming a continuous void within said head portion.

40. The self-drilling suture anchor of claim 38, wherein said means to engage with a driver comprises a cutout within said head portion and said anchoring means is incorporated within an internal portion of said head portion, said cutout and said anchoring means forming a continuous void within said head portion.

41. The self-drilling suture anchor of claim 38, wherein said means to engage with a driver comprises a square shaped cutout within said head portion and said anchoring means is incorporated within an internal portion of said head portion, said square shaped cutout and said anchoring means forming a continuous void within said head portion.

42. The self-drilling suture anchor of claim 38, wherein said at least one surface comprises a peripheral surface of said head portion, and said anchoring means comprises a track incorporated around said peripheral surface of said head portion.

43. The self-drilling suture anchor of claim 42 further comprising a port intersecting said track and providing an anchor point for a suture on said track.

44. The self-drilling suture anchor of claim 38, wherein said at least one surface comprises an underside surface of said head portion, and said anchoring means comprises a track incorporated within said head portion beneath said underside surface.

45. The self-drilling suture anchor of claim 38, wherein said elongate member comprises a low carbon, corrosion-resistant, non-magnetic material.

46. The self-drilling suture anchor of claim 38, wherein said elongate member comprises a reabsorbable implant material.

47. The self-drilling suture anchor of claim 38, wherein said elongate member comprises Titanium.

48. The self-drilling suture anchor of claim 38, wherein said elongate member comprises cobalt chrome.

49. The self-drilling suture anchor of claim 38, wherein said elongate member comprises stainless steel.

50. The self-drilling suture anchor of claim 38, wherein said elongate member comprises a bone screw that can be removed and reinserted without damaging substrate.

51. The self-drilling suture anchor of claim 38, wherein said elongate member comprises a bone screw sized for insertion into a particular anatomical area.

52. The self-drilling suture anchor of claim 38, further comprising a surgical plate, said surgical plate attached to the substrate by said elongate member.

53. A self-retaining suture anchor comprising:
an elongate member having a first end and a head portion, said first end adapted for insertion into a substrate;
said head portion comprising:
means to engage with a driver;
a first cleat member positioned on a first side of said means to engage with a driver; and
a second cleat member positioned on a second side of said means to engage with a driver, said first cleat member and said second cleat member operative to anchor suture;
wherein at least one of said first cleat member and said second cleat member provides a locking force between said driver and said head portion.

54. The suture anchor of claim 53, wherein said means to engage with a driver comprises a slot within said head portion.

55. The suture anchor of claim 53, wherein said means to engage with a driver comprises transverse slots within said head portion, and said first cleat member and said second cleat member are positioned on opposites sides of one of said transverse slots.

56. The suture anchor of claim 53, wherein said means to engage with a driver comprises a cutout within said head portion, and said first cleat member and said second cleat member are positioned on opposites sides of said cutout.

57. The suture anchor of claim 53, wherein said elongate member comprises a low carbon, corrosion-resistant, non-magnetic material.

58. The suture anchor of claim 53, wherein said elongate member comprises a reabsorbable implant material.

59. The suture anchor of claim 53, wherein said elongate member comprises Titanium.

60. The suture anchor of claim 53, wherein said elongate member comprises stainless steel.

61. The suture anchor of claim 53, wherein said elongate member comprises cobalt chrome.

62. The suture anchor of claim 53, wherein said elongate member comprises a bone screw that can be removed and reinserted without damaging substrate.

63. The suture anchor of claim 53 wherein said first end comprises a tapered self-tapping portion.

64. The suture anchor of claim 53 wherein said first end comprises a tapered self-drilling portion.

65. The suture anchor of claim 53 wherein said elongate member comprises a threaded portion.

66. The suture anchor of claim 53 wherein said elongate member comprises a barbed portion.

67. An apparatus for preventing suture from releasing from a suture anchor, said suture anchor comprising a head portion having at top surface and comprising a means to engage with a driver, and at least one arm formed within said head portion adjacent said means to engage, said at least one arm providing a locking force between said head portion and a driver, said apparatus comprising a plug shaped for insertion into said means to engage with a driver, said plug operative to prevent release of suture positioned below said at least one arm, said locking force operative to secure said plug within said means to engage.

68. The apparatus of claim 67, wherein said means to engage with a driver comprises a slot within said head portion, said plug having a rectangular shape and sized for insertion into said slot.

69. The apparatus of claim 67, wherein said means to engage with a driver comprises transverse slots within said head portion, said plug having rectangular shape and sized for insertion into one of said transverse slots.

70. The suture anchor of claim 67, wherein said means to engage with a driver comprises a cutout within said head portion, said plug having a shape matching a shape of said cutout and sized for insertion into said cutout.

71. A suture anchor comprising:
an elongate member having a first end and a head portion, said first end adapted for insertion into a substrate, said head portion having at least one surface and comprising means to engage with a driver; and
a track formed within said head portion below said at least one surface, said track operative to anchor at least one suture without through threading.

72. The suture anchor of claim 71, wherein said means to engage with a driver comprises a slot within said head portion and said track is incorporated within an internal portion of said head portion to one side of the slot, said slot and said track forming a continuous void within said head portion.

73. The suture anchor of claim 71, further comprising a second track formed within said head portion below said at least one surface.

74. The suture anchor of claim 72, wherein said means to engage with a driver comprises a slot within said head portion and said track and said second track are incorporated within an internal portion of said head portion on opposite sides of the slot, said slot, said track and said second track forming a continuous void within said head portion.

75. The suture anchor of claim 72, wherein said means to engage with a driver comprises transverse slots within said head portion and said track and said second track are incorporated within an internal portion of said head portion on opposite sides of one of the slots, said slots, said track and said second track forming a continuous void within said head portion.

76. The suture anchor of claim 71, wherein said means to engage with a driver comprises a cutout within said head portion and said track is incorporated within an internal portion of said head portion through said cutout and said cutout and said track forming a continuous void within said head portion.

77. The suture anchor of claim 71, wherein said means to engage with a driver comprises a square shaped cutout within said head portion and said track is incorporated within an internal portion of said head portion through said square shaped cutout, said square shaped cutout and said track forming a continuous void within said head portion.

78. The suture anchor of claim 71, wherein said at least one surface comprises a peripheral surface of said head portion, and said track is incorporated around said peripheral surface of said head portion.

79. The suture anchor of claim 78 further comprising a port intersecting said track and providing an anchor point for a suture on said track.

80. The suture anchor of claim 71, wherein said at least one surface comprises an underside surface of said head portion, and said track is incorporated within said head portion beneath said underside surface.

81. The suture anchor of claim 71, wherein said elongate member comprises a low carbon, corrosion-resistant, non-magnetic material.

82. The suture anchor of claim 71, wherein said elongate member comprises a reabsorbable implant material.

83. The suture anchor of claim 71, wherein said elongate member comprises Titanium.

84. The suture anchor of claim 71, wherein said elongate member comprises stainless steel.

85. The suture anchor of claim 71, wherein said elongate member comprises cobalt chrome.

86. The suture anchor of claim 71, wherein said elongate member comprises a bone screw that can be removed and reinserted without damaging substrate.

87. The suture anchor of claim 71, wherein said elongate member comprises a bone screw sized for insertion into a particular anatomical area.

88. The suture anchor of claim 71 wherein said first end comprises a tapered self-tapping portion.

89. The suture anchor of claim 71 wherein said first end comprises a self-drilling portion.

90. The suture anchor of claim 71 wherein said elongate member comprises a threaded portion.

91. The suture anchor of claim 71 wherein said elongate member comprises a barbed portion.

* * * * *